US008155408B2

(12) United States Patent
Ranga et al.

(10) Patent No.: US 8,155,408 B2
(45) Date of Patent: Apr. 10, 2012

(54) STANDARDIZED NORMAL DATABASE HAVING ANATOMICAL PHASE INFORMATION

(75) Inventors: Ramakanth Vengala Ranga, Bangalore (IN); Gopal Biligeri Avinash, Menomonee Falls, WI (US); Shibu Prabhakaran Pillai, Bangalore (IN); Peter Lehel, Oconomowoc, WI (US); Saad Sirohey, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 999 days.

(21) Appl. No.: 12/103,314

(22) Filed: Apr. 15, 2008

(65) Prior Publication Data

US 2009/0257628 A1 Oct. 15, 2009

(51) Int. Cl.
*G06K 9/46* (2006.01)
(52) U.S. Cl. ...................................... 382/128
(58) Field of Classification Search .............. 382/128, 382/130; 128/920, 922
See application file for complete search history.

(56) References Cited

U.S. PATENT DOCUMENTS

| | | | | |
|---|---|---|---|---|
| 7,314,446 B2* | 1/2008 | Byrd et al. | .............. | 600/443 |
| 7,327,872 B2* | 2/2008 | Vaillant et al. | .............. | 382/154 |
| 7,846,456 B2* | 12/2010 | Brin et al. | .............. | 424/236.1 |
| 2003/0048931 A1* | 3/2003 | Johnson et al. | .............. | 382/128 |

OTHER PUBLICATIONS

Iskandrian et al., M.S.: Nuclear Cardiac Imaging: Principles and Applications, 3rd Edition, Oxford University Press, New York, NY, 2002, pp. 80-81.
Van Train et al., Quantitative Same-Day Rest-Stress Technetium-99mm-Sestamibi Spect: Definition and Validation of Stress Normal Limits and Criteria for Abnormality, The Journal of Nuclear Medicine, vol. 34, No. 9, Sep. 1993, pp. 1494-1502.
Minoshima et al, A Diagnostic Approach in Alzheimer's Disease Using Three-Dimensional Stereotactic Surface Projections of Flourine-18-FDG PET, The Journal of Nuclear Medicine, vol. 36, No. 7, Jul. 1995, pp. 1238-1248.

* cited by examiner

*Primary Examiner* — Clayton E Laballe
*Assistant Examiner* — Leon W Rhodes, Jr.
(74) *Attorney, Agent, or Firm* — Ziolkowski Patent Solutions Group, SC

(57) ABSTRACT

A method for detecting a disease state is presented. In accordance with aspects of the present technique, a method for detecting a disease state is presented. The method includes creating a normal standardized data repository, where the normal standardized data repository includes one or more normal reference surface projections, where the normal reference surface projections include anatomical information obtained from one or more groups at different phases corresponding to one or more regions of interest in a normal organ, where each of the one or more groups includes one or more subjects having normal organs, and where the normal standardized data repository may be configured to aid in the detection of a disease state. Systems and computer-readable medium that afford functionality of the type defined by this method are also contemplated in conjunction with the present technique.

25 Claims, 15 Drawing Sheets

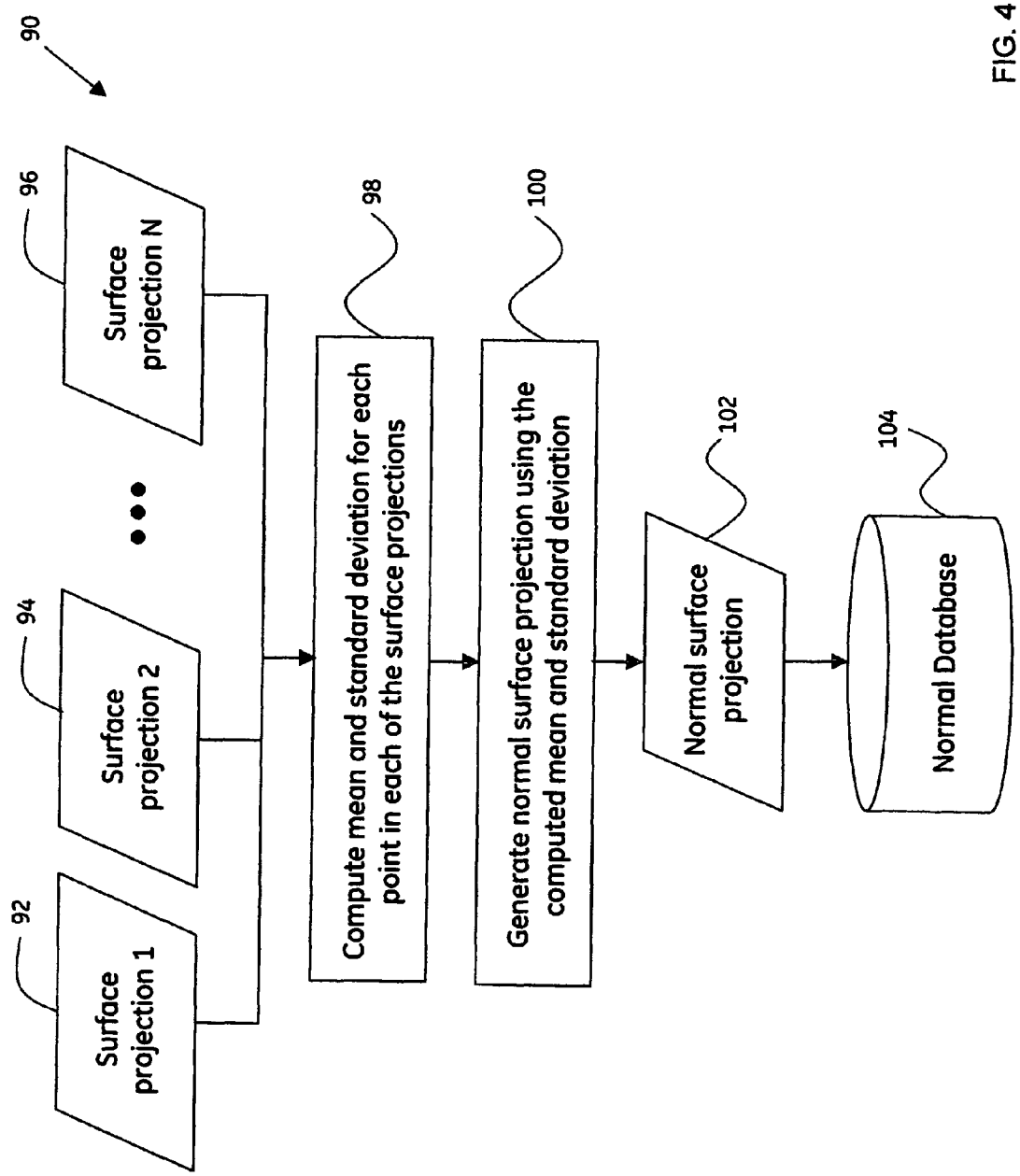

STANDARDIZED NORMAL DATABASE HAVING ANATOMICAL PHASE INFORMATION

BACKGROUND

This disclosure relates generally to diagnostic systems, and more particularly, to systems and methods for diagnosis of disease states.

Coronary artery disease (CAD) is a leading cause of death in the developed world. As will be appreciated, CAD is generally caused by the gradual buildup of fatty deposits in the coronary arteries (atherosclerosis), which slowly narrows the blood flow through the arteries. Eventually, diminished blood flow may cause chest pain (angina), shortness of breath or other symptoms. A complete blockage may cause a heart attack. Furthermore, CAD typically develops over an extended period of time, and hence may go virtually unnoticed until it produces a heart attack. Early detection is important in order to maintain the current 1-year relative survival rate after treatment of about 91%.

Coronary angiography enables the detection of blockages or obstructions. However, coronary angiography is an invasive exam, which would be prohibitive to be applied to a large asymptomatic population for the purpose of early detection of the disease. Although, coronary angiography is considered to be the "gold standard" for the detection of CAD, recently, data increasingly supports the importance of non-invasively assessing the functional definition of the severity and extent of the disease process.

Moreover, there exist several techniques for myocardial image analysis, where the techniques are typically configured to compare an image with a corresponding normal reference image and provide statistical deviations of the image from the normal reference image. Normal patient data is acquired from different patients having normal hearts under different categories, such as, but not limited to, a study type (stress/rest), a tracer, sex, or the like. Averaging all subjects in that particular category may generate a normal reference image corresponding to a particular category. These normal reference images may be stored in a database, generally referred to as a normal reference database or a normal database. Polar maps corresponding to an image may be generated and compared with a corresponding normal reference image. Contrasting regions in the polar map may indicate deviations from the normal reference database. For example, a numerical entry in a segment may indicate that stress uptake was outside normal limits in that segment. This numerical entry may correspond to a difference between rest and stress defect, for instance.

Unfortunately, the normal reference images generated by the presently available techniques fail to account for any deviations in the orientations of the anatomical organ, thereby resulting in diminished accuracy of diagnosis of disease states. Moreover, indices representative of statistical deviations of the image from the normal reference image may enable a clinician to only make a subjective call regarding the degree of severity of the disease.

As will be appreciated, different phases may be associated with various anatomical organs. By way of example, if the anatomical organ includes the heart, the different phases of the heart may include a systolic phase, a diastolic phase, and phases therebetween. The presently available techniques fail to include information regarding the different phases of an organ. Consequently, the presently available techniques fail to account for the different phases of the anatomical organs, thereby leading to diminished accuracy of diagnosis of disease states.

It may therefore be desirable to develop a design that allows enhanced diagnosis of disease states. More particularly, there exists a need for generating normal reference images that account for the different phases of an anatomical organ, thereby allowing enhanced comparison between images and the corresponding normal reference images, thereby enhancing clinical workflow. In addition, there is also a need for generating normal reference images that account for any deviations in orientation of an anatomical region of interest.

BRIEF DESCRIPTION

In accordance with aspects of the present technique, a method for detecting a disease state is presented. The method includes creating a normal standardized data repository, where the normal standardized data repository includes one or more normal reference surface projections, where the normal reference surface projections include anatomical information obtained from one or more groups at different phases corresponding to one or more regions of interest in a normal organ, where each of the one or more groups includes one or more subjects having normal organs, and where the normal standardized data repository may be configured to aid in the detection of a disease state. Computer-readable medium that afford functionality of the type defined by this method is also contemplated in conjunction with the present technique.

In accordance with further aspects of the present technique, a method for detecting a disease state is presented. The method includes obtaining image data corresponding to a plurality of phases associated with a normal organ from a plurality of normal subjects. Furthermore, the method includes extracting image data corresponding to a region of interest within the normal organ from the obtained image data to generate one or more extracted image data sets corresponding to each of the plurality of phases associated with the region of interest. The method also includes standardizing the extracted image data sets to generate standardized image data sets. In addition, the method includes generating a standardized surface projection corresponding to each of the standardized image data sets associated with the region of interest for each of the plurality of phases for each of the plurality of normal subjects. Also, the method includes normalizing the standardized surface projection corresponding to each of the standardized image data sets associated with the region of interest for each of the plurality of phases for each of the plurality of normal subjects to generate a standardized and normalized surface projection corresponding to each of the standardized surface projection associated with the region of interest for each of the plurality of phases for each of the plurality of normal subjects. Moreover, the method includes computing a mean, a standard deviation, or a combination thereof, based on the generated standardized and normalized surface projections associated with each of the plurality of phases for the plurality of normal subjects. Additionally, the method includes generating a normal reference surface projection corresponding to each of the plurality of phases associated with the region of interest employing the corresponding computed mean, the computed standard deviation, or a combination thereof, where the normal reference surface projections are representative of the plurality of phases associated with the region of interest in the normal organ.

In accordance with another aspect of the present technique, a method for detecting a disease state is presented. The method includes obtaining image data corresponding to a plurality of phases associated with an organ from a subject. In addition, the method includes generating a standardized and normalized surface projection corresponding to each of the plurality of phases associated with the organ. The method also includes obtaining a corresponding normal reference surface projection associated with each of the plurality of phases from a normal standardized data repository. Furthermore, the method includes comparing each of the standardized surface projections with a corresponding normal reference surface projection to facilitate detection of a disease state.

In accordance with yet another aspect of the present technique, a processing platform is presented. The processing platform includes an image data acquiring module configured to acquire image data corresponding to a plurality of phases associated with an organ. Furthermore, the processing platform includes a segmentation module configured to extract image data corresponding to a region of interest in the organ from the obtained image data to generate one or more extracted image data sets corresponding to each of the plurality of phases associated with the region of interest in the organ, standardize the extracted image data sets to generate standardized image data sets, generate a standardized surface projection corresponding to each of the standardized image data sets associated with the region of interest in the organ for each of the plurality of phases for the subject, and normalize the standardized surface projection corresponding to each of the standardized image data sets associated with the region of interest in the organ for each of the plurality of phases for the subject to generate a standardized and normalized surface projection corresponding to each of the standardized image data sets associated with the region of interest in the organ for each of the plurality of phases for the subject. Additionally, the processing platform includes a normal generator module configured to generate a normal reference surface projection corresponding to each of the plurality of phases using the standardized and normalized surface projections, and generate a normal standardized data repository using the normal reference surface projections, where the normal standardized data repository includes one or more normal reference surface projections. Moreover, the processing platform also includes a diagnosis module configured to aid in comparing a standardized and normalized surface projection associated with a current subject with a corresponding normal reference surface projection to facilitate detection of a disease state, where the diagnosis module is configured to generate a surface projection representative of any statistical deviation of the current standardized and normalized surface projection from the corresponding normal reference surface projection.

In accordance with yet another aspect of the present technique, a system is presented. The system includes an imaging system configured to aid in acquisition of image data, where the image data is representative of an organ in a subject. Further, the system also includes a processing platform configured to aid in processing the acquired image data, where the processing platform includes an image data acquiring module configured to acquire image data corresponding to a plurality of phases associated with the organ, a segmentation module configured to extract image data corresponding to a region of interest in the organ from the obtained image data to generate one or more extracted image data sets corresponding to each of the plurality of phases associated with the region of interest in the organ, standardize the extracted image data sets to generate standardized image data sets, generate a standardized surface projection corresponding to each of the standardized image data sets associated with the region of interest for each of the plurality of phases for the subject, and normalize the standardized surface projection corresponding to each of the standardized image data sets associated with the region of interest in the organ for each of the plurality of phases for the subject to generate a standardized and normalized surface projection corresponding to each of the standardized image data sets associated with the region of interest in the organ for each of the plurality of phases for the subject, a normal generator module configured to generate a normal reference surface projection corresponding to each of the plurality of phases using the standardized and normalized surface projections, and generate a normal standardized data repository using the normal reference surface projections, where the normal standardized data repository includes one or more normal reference surface projections. In addition, the system includes a diagnosis module configured to aid in comparing a standardized and normalized surface projection associated with a current subject with a corresponding normal reference surface projection to facilitate detection of a disease state, where the diagnosis module is configured to generate a surface projection representative of any statistical deviation of the current standardized and normalized surface projection from the corresponding normal reference surface projection. The system also includes a display module configured to display the standardized and normalized surface projection, the normal reference surface projection, the surface projections representative of any statistical deviation of the current standardized and normalized surface projection from the corresponding normal reference surface projection, other image data, or combinations thereof, to aid a clinician in the detection of a disease state.

DRAWINGS

These and other features, aspects, and advantages of the present invention will become better understood when the following detailed description is read with reference to the accompanying drawings in which like characters represent like parts throughout the drawings, wherein:

FIG. 4 is a flow chart illustrating an exemplary process of generating a standardized normal reference database, in accordance with aspects of the present technique;

DETAILED DESCRIPTION

As will be described in detail hereinafter, methods and systems for detection and/or diagnosis of a disease state are presented. Employing the methods and systems described hereinafter, clinical workflow may be dramatically enhanced by allowing a clinician to view an image representative of statistical deviation of a current standardized surface projection from a corresponding normal reference surface projection, thereby substantially enhancing the productivity of the caregivers and patient care.

It may be noted that as used herein the term "normal" anatomical organ is used to represent an anatomical organ that is free from any infection or other form of disease or malformation. Similarly, the term "normal" surface projection is used to represent a surface projection representative of a normal anatomical region of interest within a normal anatomical organ. In addition, the term "normal" data depository or "normal" reference data repository or "normal" database may be used to represent a database or data repository of "normal" surface projections.

Although, the exemplary embodiments illustrated hereinafter are described in the context of a medical imaging system, it will be appreciated that use of the system in industrial applications are also contemplated in conjunction with the present technique. For example, the exemplary embodiments may be employed to monitor progression of a crack in a gas pipeline or an oilrig.

Figure 1:
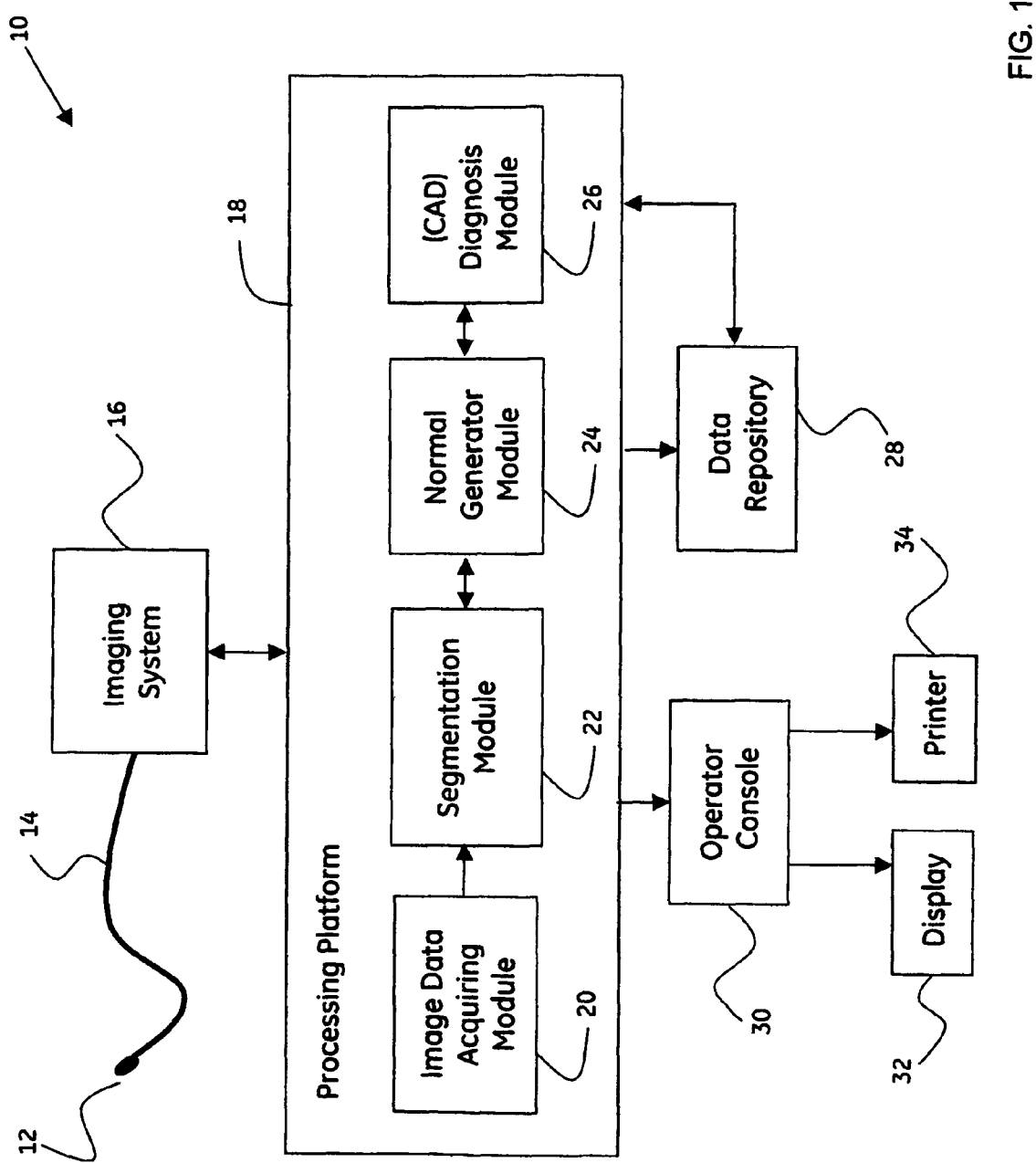
FIG. 1 is a diagrammatic illustration of a diagnostic system, in accordance with aspects of the present technique.

FIG. 1 is a block diagram of an exemplary system 10 for use in diagnostic imaging in accordance with aspects of the present technique. More particularly, the system 10 may be configured to facilitate detection and/or diagnosis of a disease state in a patient. As will be appreciated by one skilled in the art, the figures are for illustrative purposes and are not drawn to scale.

The system 10 may be configured to acquire image data from a patient 12 via an image acquisition device 14. In one embodiment, the image acquisition device 14 may include a probe, where the probe may include an invasive probe, or a non-invasive or external probe, such as an external ultrasound probe, that is configured to aid in the acquisition of image data. Also, in certain other embodiments, image data may be acquired via one or more sensors (not shown) that may be disposed on the patient 12. By way of example, the sensors may include physiological sensors (not shown) such as electrocardiogram (ECG) sensors and/or positional sensors such as electromagnetic field sensors or inertial sensors. These sensors may be operationally coupled to a data acquisition device, such as an imaging system, via leads (not shown), for example.

The system 10 may also include an imaging system 16 that is in operative association with the image acquisition device 14. In a presently contemplated configuration, the imaging system 16 may include a medical imaging system. It may be noted that although the present example illustrates the diagnostic system 10 as including one imaging system 16, the diagnostic system 10 may include more than one imaging system.

Furthermore, it may also be noted that although the exemplary embodiments illustrated hereinafter are described in the context of a medical imaging system, other imaging systems and applications, such as industrial imaging systems, and non-destructive evaluation and inspection systems, such as pipeline inspection systems and liquid reactor inspection systems, are also contemplated. Moreover, it may be noted that although the exemplary embodiments illustrated hereinafter are described in the context of a medical imaging system, such as, but not limited to, a positron emission tomography (PET) imaging system, an optical imaging system, a computed tomography (CT) imaging system, a magnetic resonance (MR) imaging system, an X-ray imaging system, or an ultrasound imaging system, other imaging systems, such as, but not limited to, a pipeline inspection system, a liquid reactor inspection system, or other imaging systems are also contemplated in accordance with aspects of the present technique.

As previously noted, use of presently available techniques for the diagnosis of a disease state typically entails comparing a polar plot associated with a current patient with a corresponding normal reference polar plot, where the normal reference polar plot is typically stored in a data repository, such as a normal reference image database. Generally, the normal reference image database or normal database includes averaged polar plots of all subjects contained in a general sample space, where the subjects in the general sample space are understood to have normal anatomical organs, such as hearts. Contrasting regions in the polar maps may be indicative of deviations from the normal reference image. However, using these normal reference polar plots, clinicians may only make a subjective call to the degree of severity of the disease using indices representative of these deviations. In addition, the normal polar plots stored in the normal reference database fail to include phase information associated with normal anatomical organs, thereby resulting in false positives and/or false negatives and thus leading to loss of efficiency in the diagnosis of disease states. More particularly, the traditionally used normal polar plots stored in the normal database fail to account for any deviations of orientation of the anatomical organs in the current patient and the stored polar plots.

Accordingly, a system configured to facilitate enhanced diagnosis of disease states is presented. In accordance with aspects of the present technique, the system 10 may be configured to aid a clinician in the enhanced diagnosis of a disease state. More particularly, the system 10 may be configured to facilitate generation of a normal reference data repository that advantageously circumvents the shortcomings of the presently available normal reference databases. In other words, the system 10 may be configured to use anatomical information provided by high resolution images, such as PET and/or CT images, and three-dimensional (3D) information instead of the polar plots or SPECT images to perform the comparison of a patient disease state with respect to the normal reference database, in accordance with exemplary aspects of the present technique.

In accordance with aspects of the present technique, the system 10 may include a processing platform 18 that may be operatively coupled with the imaging system 16. The processing platform 18 may be configured to process the image data acquired via the imaging system 16 to facilitate the generation of a normal reference data repository, where the normal reference data repository may be configured to aid the clinician in the enhanced diagnosis of a disease state in the patient 12, if any. In certain embodiments, the normal reference data depository may be configured to include patient data corresponding to patients or subjects having normal anatomical organs. More particularly, in one embodiment, patient data may include image data corresponding to a plurality of phases associated with one or more anatomical organs in the patient 12. Furthermore, image data representative of various phases associated with normal anatomical organs may be acquired from a plurality of subjects corresponding to each group, where each group may be representative of a category or study group of subjects having normal anatomical organs.

As previously noted, presently available techniques typically store polar plots in the normal reference data repository. However, in a presently contemplated configuration, the normal reference data repository may include normal surface projections, instead of the standard polar plots. In accordance with aspects of the present technique, the surface projection may include a stereotactic surface projection, in certain embodiments. It may be noted that one or more groups of subjects having normal anatomical organs may be considered, where each of the one or more groups may include one or more subjects. Further, each of the groups may correspond to a particular normal anatomical organ. More particularly, each of the groups may correspond to different phases associated with the normal anatomical organs. It may be noted that the terms normal reference image database, a normal database, normal data repository, or normal reference data repository may be used interchangeably. By way of example, the categories or groups may include a sex, an age, a race, a test type (stress/rest), or the like. The normal reference data repository will be described in greater detail with reference to FIGS. 3-8.

As noted hereinabove, in accordance with aspects of the present technique, normal reference surface projections corresponding to different phases of a normal anatomical organ may be generated. Accordingly, the processing platform 18 may include an image data acquiring module 20 configured to aid in acquiring image data corresponding to the different phases of a normal anatomical organ. It may be noted that the anatomical organ may include a dynamic anatomical organ, a static anatomical organ, or a combination thereof. The dynamic anatomical organ may include the heart, the lungs, the liver, or the like, while the static anatomical organ may include a kidney, a brain, or the like. As will be appreciated, the dynamic anatomical organ may experience a regular and/or irregular motion, thereby resulting in different phases associated with the motion of the dynamic anatomical organ. For example, the heart may include a systolic phase, a diastolic phase, and phases therebetween. Furthermore, as will be appreciated, the static anatomical organ may not experience any regular and/or irregular motion. Accordingly, different phases corresponding to the static anatomical organ may be configured to include movement of a contrast agent disposed in the patient 12 through the static anatomical organ in the patient 12, for instance. The working of the image data acquiring module 20 will be described in greater detail with reference to FIGS. 3-8.

Additionally, the processing platform 18 may also include a segmentation module 22. The segmentation module 22 may be configured to process the image data acquired by the image data acquiring module 20. More particularly, the segmentation module 22 may be configured to extract image data associated with a desired region of interest in the scanned normal organ from the image data acquired by the image data acquiring module 20. The segmentation module 22 may also be configured to standardize the extracted image data. In other words, the segmentation module 22 may be configured to align the extracted image data to a standardized reference space. Additionally, the segmentation module 22 may also be configured to employ the standardized image data set to generate a surface projection corresponding to the region of interest in the scanned normal organ. The working of the segmentation module 22 will be described in greater detail with reference to FIGS. 3-8.

Subsequently, the surface projections corresponding to the various phases associated with the region of interest in the scanned normal organ generated by the segmentation module 22 may then be processed by a normal generator module 24. In other words, a plurality of standardized surface projections may be generated by the segmentation module 22, where the standardized surface projections correspond to the different phases of the region of interest in the scanned normal organ and where the standardized surface projections may be associated with one or more subjects in a group. The normal generator module 24 may be configured to process the standardized surface projections associated with a group of subjects and corresponding to a particular phase of the region of interest in the scanned normal organ to generate a normal surface projection that is representative of a particular phase associated with a normal anatomical region of interest in a particular group of subjects. Normal surface projections corresponding to other phases associated with the anatomical region of interest for the particular group may also be generated. In a similar fashion, normal surface projections corresponding to other regions of interest in the scanned normal organ may also be generated.

This process may be repeated for each group of sample subjects, thereby resulting in a plurality of normal surface projections corresponding to each group in the sample space. These normal surface projections may then be employed to generate a normal reference data repository 28 or normal database. The working of the normal generator module 24 will be described in greater detail with reference to FIGS. 3-8.

The processing platform 18 may also include a diagnosis module 26, where the diagnosis module 26 may be configured to aid in computer aided diagnosis of a disease state in the patient 12. More particularly, the diagnosis module 26 may be configured to aid the clinician in diagnosing a disease state in the patient 12. In other words, the diagnosis module 26 may be configured to retrieve a normal reference surface projection corresponding to each of the different phases of the region of interest from the normal data repository 28. Additionally, the diagnosis module 26 may be configured to compare standardized surface projections associated with the different phases of the region of interest in the scanned organ of the current patient 12 with the corresponding retrieved normal surface projections, thereby allowing identification and/or diagnosis of any disease states. The working of the diagnosis module 26 will be described in greater detail with reference to FIGS. 3-8.

In addition, the processing platform 18 may be accessed and/or operated via an operator console 30. The operator console 30 may also be employed to facilitate the display of acquired images and/or the results of the comparison between the current standardized surface projection and the corresponding retrieved normal surface projection generated by the processing module 18, such as on a display 32 and/or a printer 34. For example, an operator, such as a clinician, may use the operator console 30 to designate the manner in which results of the comparison are visualized on the display 32.

Figure 2:
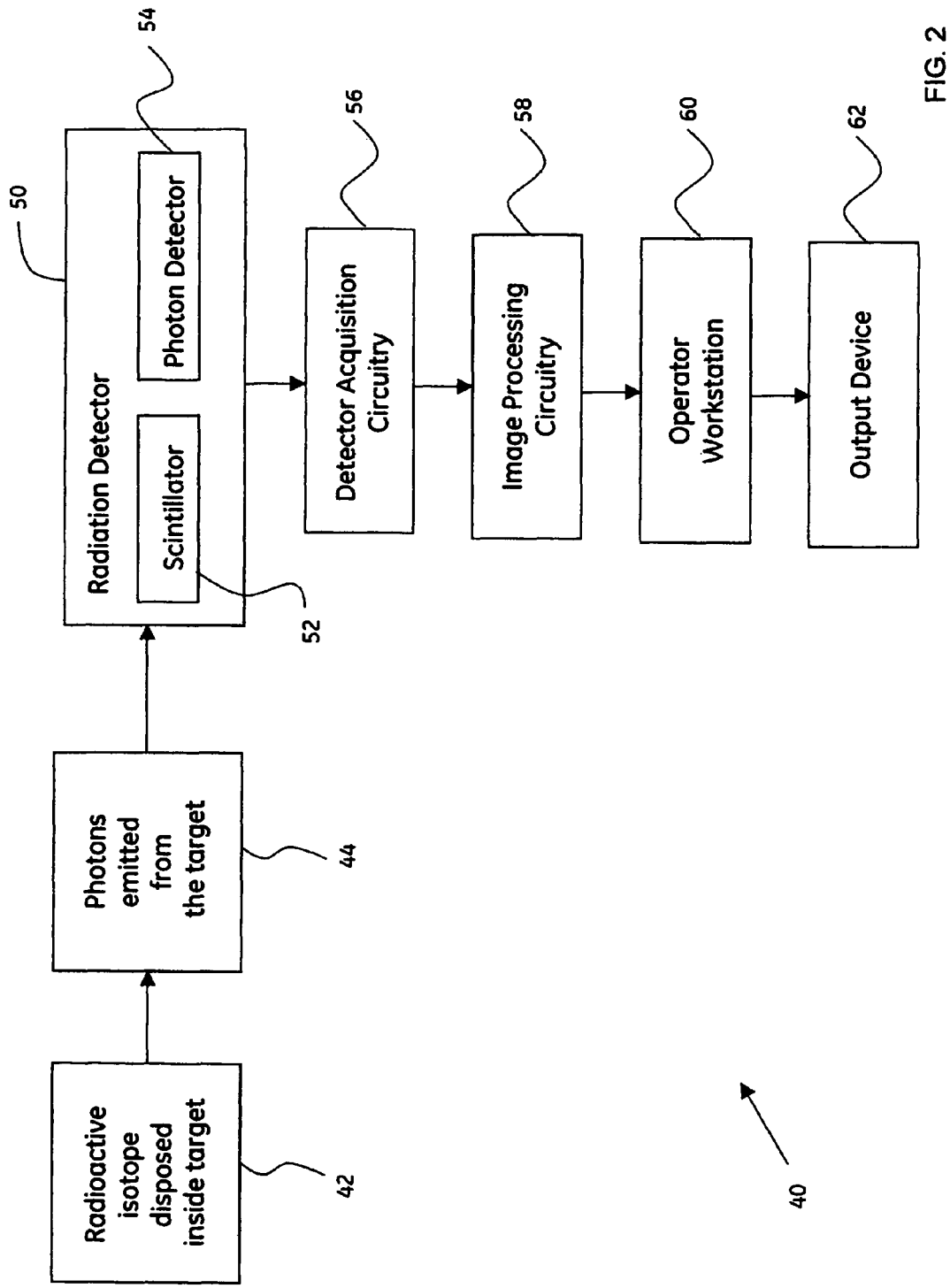
FIG. 2 is a block diagram of an exemplary imaging system in the form of a positron emission tomography (PET) imaging system for use in the exemplary diagnostic system of FIG. 1.

As previously noted with reference to FIG. 1, the medical imaging system 16 may include a PET imaging system. FIG. 2 is a block diagram showing an imaging system 40 for acquiring and processing image data. More particularly, FIG. 2 illustrates a radiation-based imaging system 40, such as a PET imaging system. In the illustrated embodiment, the PET imaging system 40 includes a radioactive substance 42 disposed within a target. In one embodiment, the target may be a human, such as the patient 12 (see FIG. 1), having an injection of a radioactive tracer. Typically, the radioactive tracer is administered to desired locations inside the patient 12 by tagging it along with a natural body compound, such as glucose, ammonia, water, or the like. In general, after the dose of the radioactive tracer is administered inside the target, such as the patient 12, the radioactive substance, during its lifetime, emits radiation 44 that is detected by the radiation detector 50 (scintillator 52 and photon detector 54). Once inside the target, the radioactive substance 42 localizes the radioactivity in the biologically active areas or other areas to be detected. In an exemplary embodiment, where the target is a human or an animal, the biologically active areas may include a cerebral or cardiac profusion, Alzheimer, Parkinson, epilepsy, hibernating myocardium, cancer, or tumor. Typically, a dose of the radioactive substance 42 includes a radioactive tracer, which emits positrons and is disposed inside a target in a function-specific or tissue-specific manner. As will be appreciated by those skilled in the art, the positron emitted from the radioactive tracer annihilates by reaction with electrons to produce two photons or two gamma rays each having energy of 511 KeV. These photons then penetrate out of the target and are detected via the radiation detector 50, i.e., the PET scanner.

In the illustrated embodiment, the radiation detector or the PET scanner 50 may include a scintillator 52. Attenuated radiation from the target may impinge on one or more radiation detectors 50, which include a scintillator 52 that produces visible photons in response to the impinging attenuated radiation on its surface.

With continuing reference to FIG. 2, once the scintillator 52 produces the photons, the photons may be detected by employing a photon detector or counter 54. In some embodiments, the photon detector 54 may include a photodiode configured to convert the photons into respective electronic signals. Also, in some of these embodiments, the photon detector 54 may be coupled to a photomultiplier tube to proportionately enhance the signals produced by the photon detector 54. The PET imaging system 40 may then process this data to construct an image of the internal features within the target (patient 12). Although not illustrated, the radiation detector 50 may employ a collimator for collimating beams directed towards the radiation detector 50 and, thereby, enhance the absorption percentage of the incident light on the radiation detector 50. In addition, the PET imaging system 40 of FIG. 2 may include a variety of control circuits and devices. For example, as illustrated, the radiation detector 50 is operationally coupled to detector acquisition circuitry 56, which controls acquisition of the signals generated in the radiation detector 50. In certain embodiments, the PET imaging system 40 may include a motor subsystem (not shown) to facilitate motion of the radiation detector 50. In these embodiments, image processing circuitry 58 may be employed to execute examination of protocols and to process acquired image data from the detector acquisition circuitry 56. These and various other control mechanisms may be incorporated into the imaging system 40.

As an interface to the PET imaging system 40, one or more operator workstations 60 may be included for outputting system parameters, requesting examination, viewing images, and so forth. The operator workstation 60 may be configured to enable an operator, via one or more input devices (keyboard, mouse, touch pad, etc.), to control one or more components of the PET imaging system 40. In one embodiment, the operator workstation 60 may include the operator console 30 (see FIG. 1). The illustrated operator workstation 60 is shown as being coupled to an output device 62, such as a display or printer, to output the images generated during operation of the imaging system 40. Here again, in certain embodiments, the output device 62 may include the display 32 (see FIG. 1) and/or the printer 34 (see FIG. 1). In general, displays, printers, operator workstations, and similar devices may be local or remote from the PET imaging system 40. For example, these interface devices may be positioned in one or more places within an institution or hospital, or in an entirely different location. Therefore, the interface devices may be linked to the PET imaging system 40 via one or more configurable networks, such as the Internet, virtual private networks, and so forth. These and other input/output devices or interfaces may be incorporated into the PET imaging system 40.

Figure 3:
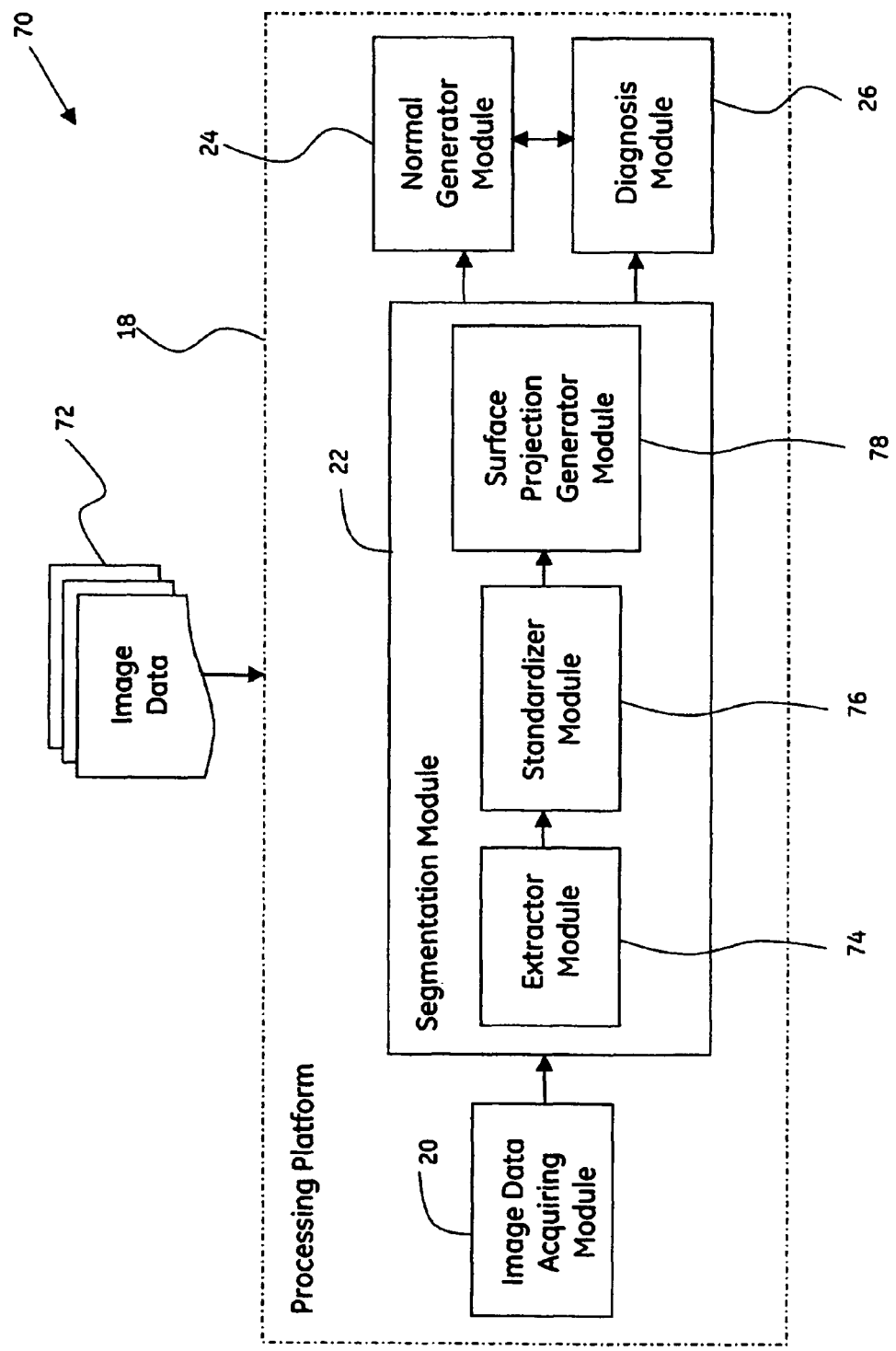
FIG. 3 is a block diagram of a portion of the exemplary diagnostic system of FIG. 1, in accordance with aspects of the present technique.
Figure 5A:
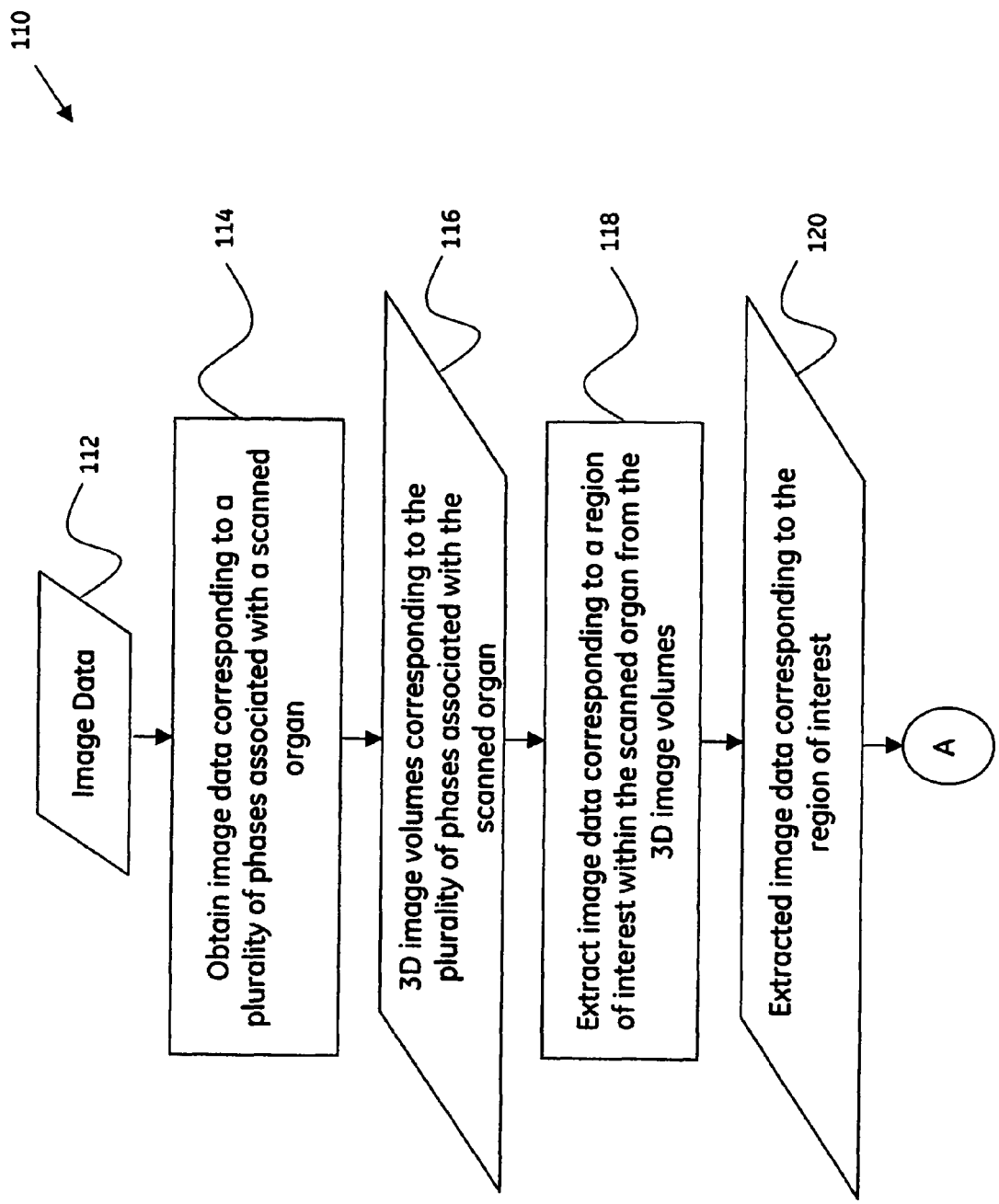
FIGS. 5A-5E are flow charts illustrating an exemplary process of generating a normal reference database, in accordance with aspects of the present technique.
Figure 5B:
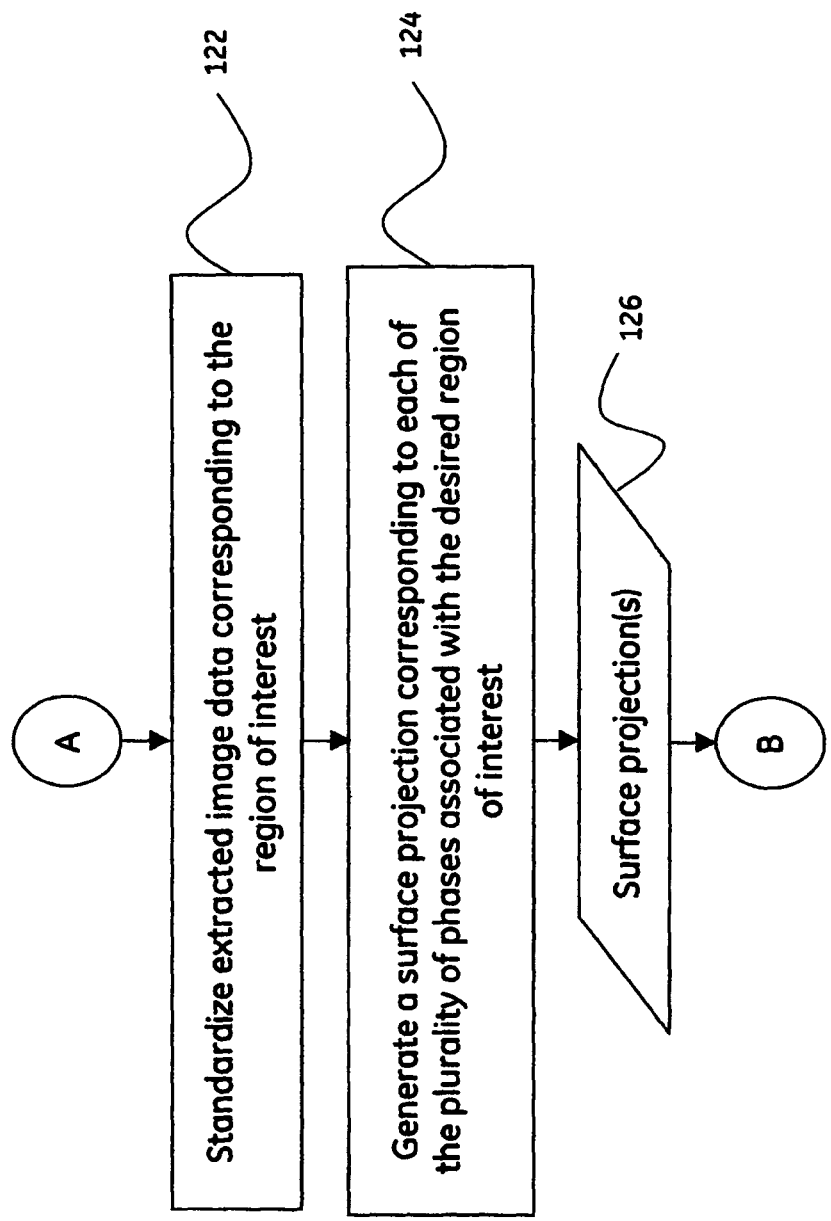
Figure 5C:
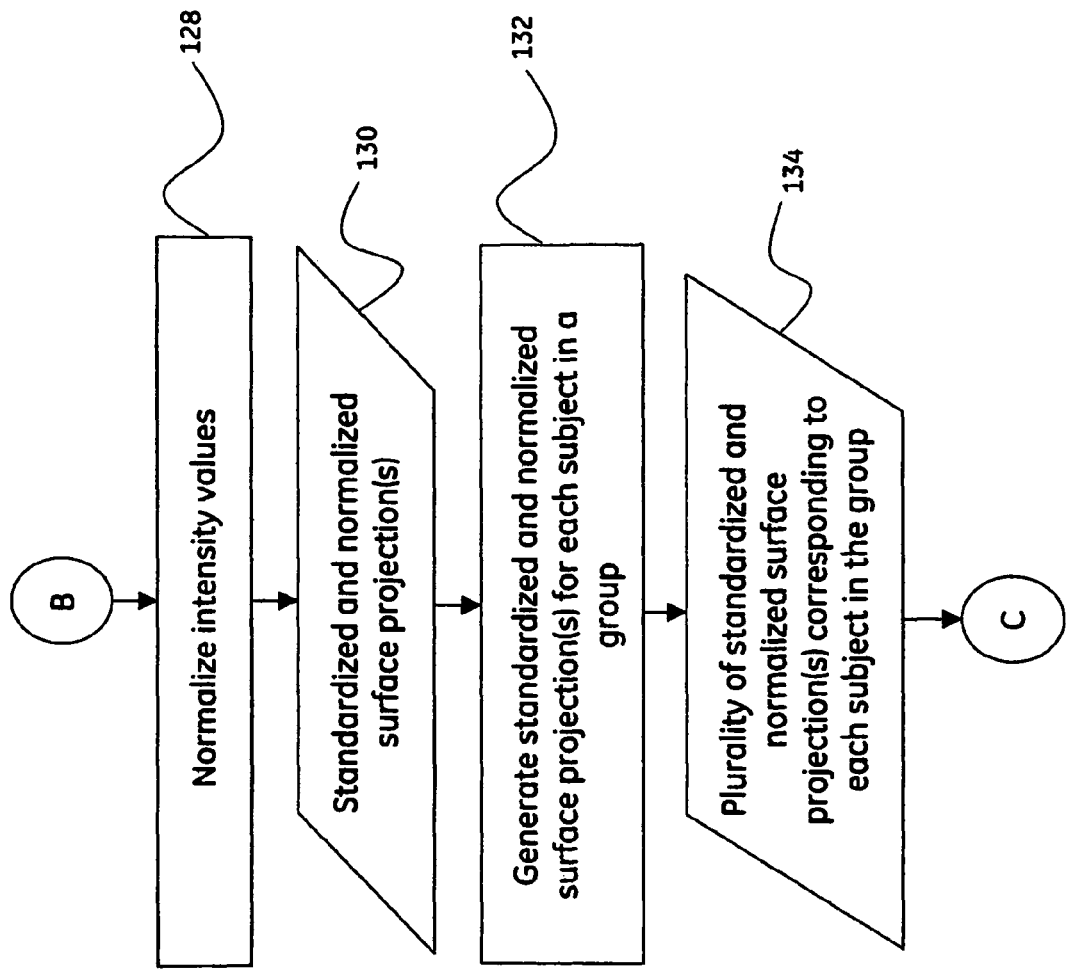
Figure 5D:
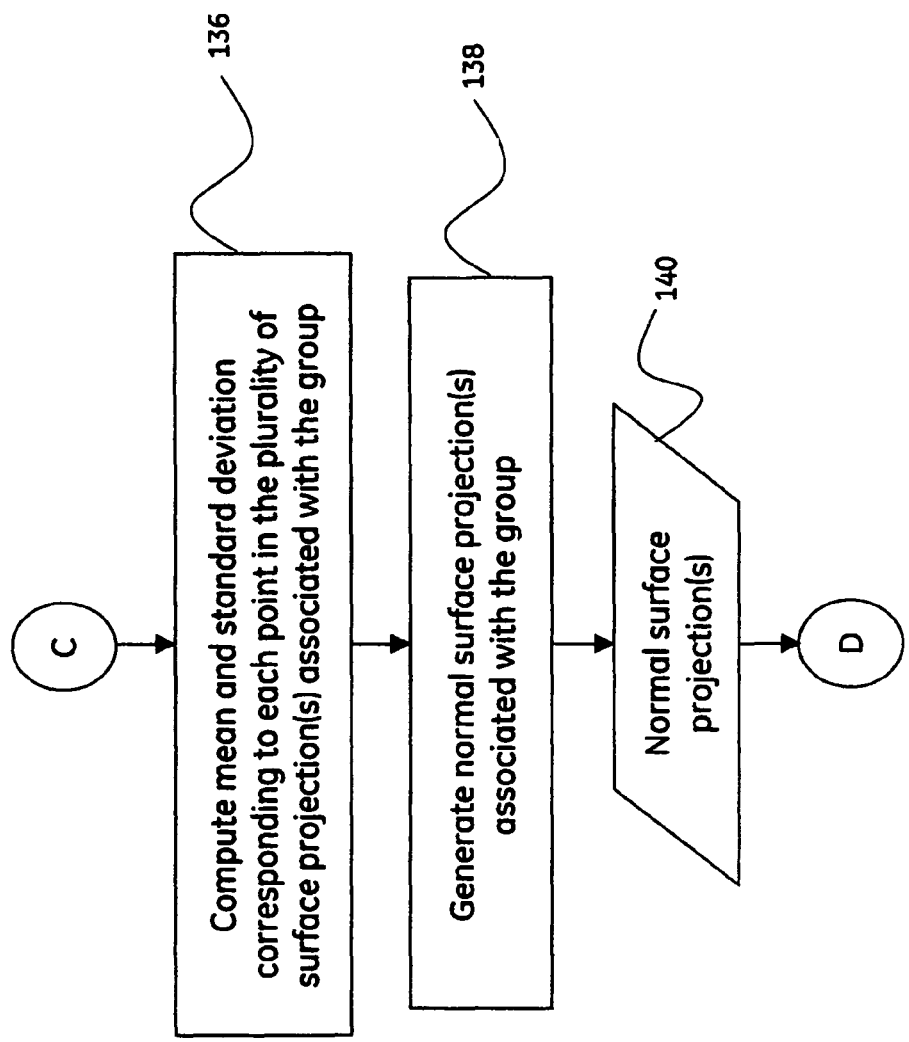
Figure 5E:
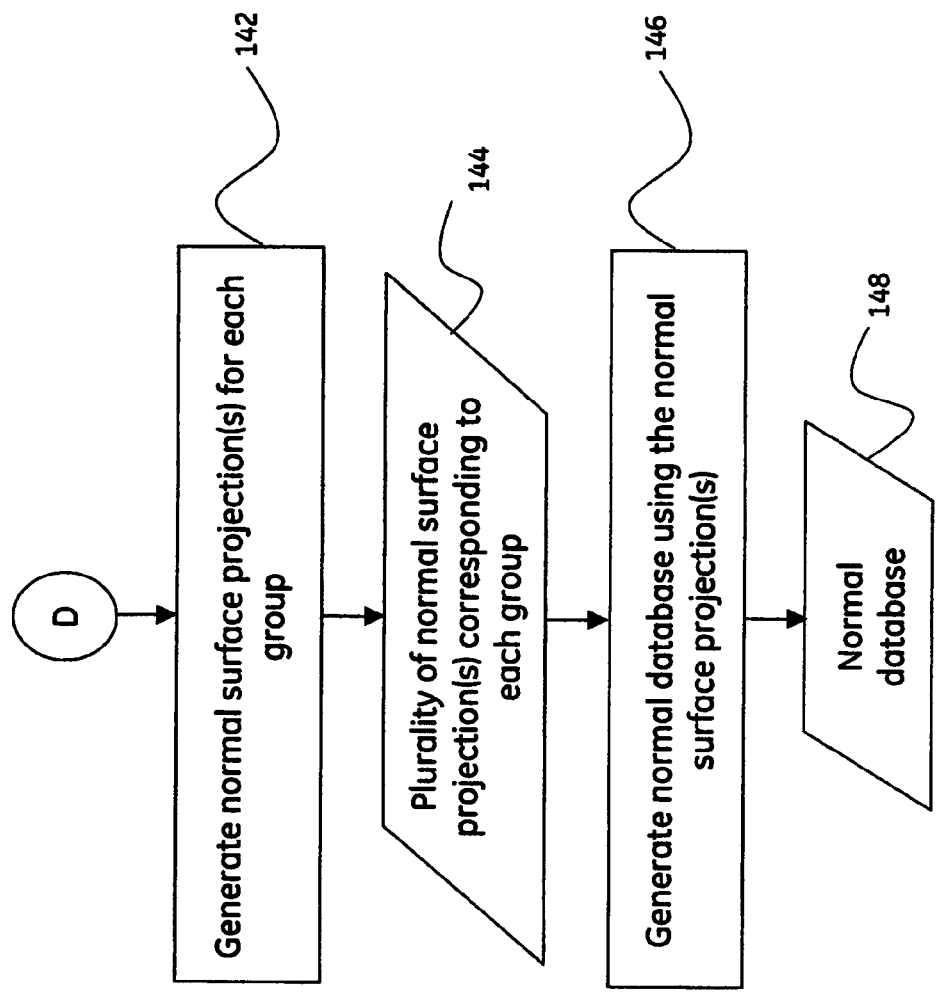

Referring now to FIG. 3, a block diagram 70 of one embodiment of the processing platform 18 (see FIG. 1) is depicted. Also, as previously noted, the processing platform 18 may be configured to aid in the generation of a normal reference data repository, such as the normal data repository 28 (see FIG. 1). In addition, the processing platform 18 may include the image data acquiring module 20, the segmentation module 22, the normal generator module 24, and the diagnosis module 26, as previously noted. The image data acquiring module 20 may be configured to extract image data corresponding to different phases associated with a scanned organ from image data 72 acquired via the imaging system 16 (see FIG. 1). For example, if the image data 72 includes image data representative of a cardiac region of the patient 12 (see FIG. 1), then the image data acquiring module 20 may be configured to extract images corresponding to a systolic phase, a diastolic phase, and phases therebetween of the heart from the image data 72. It may be noted that, in certain embodiments, consequent to processing by the image data acquiring module 20, three-dimensional (3D) image volumes corresponding to the plurality of phases associated with the scanned organs may be generated.

Subsequently, the 3D image volumes generated by the image data acquiring module 20 may be processed via the segmentation module 22. In a presently contemplated configuration, the segmentation module 22 is shown as including an extractor module 74, a standardizer module 76, and a surface projection generator module 78. The extractor module 74 may be configured to extract image data corresponding to a desired region in the scanned organ from the 3D image volumes. For example, if the image data 72 includes image data representative of a cardiac region of the patient 12 (see FIG. 1), the image data acquiring module 20 may be configured to extract image data corresponding to the systolic phase, the diastolic phase and phases therebetween. Subsequently, the extractor module 74 may be configured to extract image data corresponding to a desired region of interest in the cardiac region, such as the left ventricle, from the 3D image volumes generated by the image data acquiring module 20. Consequent to processing by the extractor module 74, extracted image data corresponding to the desired region of interest in the scanned organ may be generated.

Furthermore, the segmentation module 22 may also include the standardizer module 76, as previously noted. The standardizer module 76 may be configured to "standardize" the extracted image data corresponding to the desired region of interest that has been extracted by the extractor module 74. As used herein, the term standardize is used to refer to alignment of the extracted image data with a standardized reference space. It may be noted that the terms reference space and atlas space may be used interchangeably.

More particularly, the standardizer module 76 may be configured to select a reference plane in the scanned organ. The reference plane may include any arbitrary plane in the scanned organ. The standardizer module 76 may also be configured to align an orientation of the extracted image data associated with the desired region of interest with an orientation of the selected reference plane to generate an aligned image data set. An aligned image data set may be generated for each of the plurality of phases associated with the region of interest in the scanned organ. By way of example, if the scanned organ includes the heart, then the right coronary artery may be selected as the reference plane. Orientations of the extracted image data sets may be aligned with the orientation of the right coronary artery.

Moreover, the standardizer module 76 may also be configured to project the aligned image data sets to synchronize the aligned image data sets with one or more reference points in a standard space. As used herein, the term standard space is used to refer to a space having reference points and/or an atlas present. In other words, the standard space may include a predefined anatomical standard space. Accordingly, the aligned image data sets may be projected in order to synchronize the aligned image data sets with one or more reference points in the reference space. As will be appreciated aligning and standardizing the extracted image data sets with the reference space advantageously aids in circumventing any problems that may arise during registrations of anatomies during subsequent comparison steps.

Presently available techniques typically employ polar plots to aid in the detection of any disease states. As will be appreciated, polar maps images generally include two-dimensional (2D) plots of reconstructed short axis images, representing the whole of a portion of an anatomical region of interest. Also, these polar plots are typically generated by sampling different portions of the anatomical region of interest using different coordinate systems. For example, if the portion of anatomical region of interest includes the left ventricular region of the heart, then generation of polar maps typically entails use of spherical coordinate system for the apex region and the cylindrical coordinate system for the remainder of left ventricular region. Unfortunately, use of polar plots results in reduced comparison capabilities, thereby resulting in diminished detection and/or diagnosis of disease states.

The shortcomings of the presently available techniques may be advantageously circumvented via use of a surface projection associated with the extracted anatomical region of interest, in accordance with exemplary aspects of the present technique. It may be noted that surface projections may be configured to include a matrix of surface points that include the actual information associated with the anatomical region of interest, thereby allowing a more accurate comparison of a normal surface projection with an abnormal surface projection. Accordingly, the surface projection generator module 78 may be configured to generate at least one surface projection corresponding to the desired anatomical region of interest. More particularly, a surface projection corresponding to each of the plurality of phases associated with the desired region of interest may be generated. By way of example, if the desired region of interest includes the left ventricle in the heart, then surface projections corresponding to each of the systolic phase, the diastolic phase, and phases therebetween, associated with the left ventricle may be generated. In addition, surface projections corresponding to the different phases of an inner surface (endocardium) of the left ventricle may be generated. Additionally, surface projections corresponding to the different phases of an outer surface (epicardium) of the left ventricle may also be generated. It may be noted that the surface projections so generated by the surface projection generator module 78 may include three-dimensional (3D) surface projections, in certain embodiments.

Moreover, one or more standardized surface projections corresponding to the different phases associated with various anatomical regions of interest in different organs may be generated for each subject in a group. By way of example, the group or category may include a group of females in an age range from about 20 years to about 40 years, and the group may include about 40 subjects. Accordingly, a standardized surface projection corresponding to different phases of the various anatomical regions of interest may be generated for each subject in the group. In a similar fashion, standardized surface projections associated with other organs in each subject in the group may also be generated. Subsequently, the standardized surface projections may be processed to generate one "normal" surface projection, wherein the normal surface projection may be representative of the surface projections corresponding to a phase of the region of interest associated with a particular group of subjects. The normal generator module 24 may be configured to aid in generating the normal surface projection that is representative of the surface projections corresponding to a phase of the region of interest associated with a particular group of subjects.

The generation of the normal data repository and more particularly, the working of the normal generator module 24 may be better understood with reference to FIG. 4. Turning now to FIG. 4, a flow chart 90 illustrating a method of generating the normal data repository is depicted. More particularly, a method of generating the normal surface projection corresponding to a phase of an anatomical region of interest associated with a group by the normal generator module 24 (see FIG. 1) is presented.

As previously noted, the image data 72 (see FIG. 3) representative of the scanned organ(s) may be processed by the image data acquiring module 20 (see FIG. 1) to acquire image data corresponding to different phases associated with the scanned organ. Subsequently, the image data corresponding to the different phases may be processed by the extractor module 74 (see FIG. 3), the standardizer module 76, and the surface projection generator module 78 (see FIG. 3), at least one standardized surface projection corresponding to each phase associated with different anatomical regions of interest in the scanned organs for each subject in a group may be generated. This process may then be repeated for other organs in each subject in the group under consideration. By way of example, if the group includes N subjects, then at least N standardized surface projections corresponding to a phase associated with an anatomical region of interest in a particular organ may be generated subsequent to processing by the extractor module 74, the standardizer module 76, and the surface projection generator module 78. In the example illustrated in FIG. 4, a first standardized surface projection may be represented by reference numeral 92, while reference numeral 94 may be representative of a second standardized surface projection. In a similar fashion an $N^{th}$ standardized surface projection may be represented by reference numeral 96. It may be noted that the standardized surface projections 92, 94, 96 may be representative of standardized surface projections corresponding to a phase associated with an anatomical region of interest in the scanned organ. For example, the standardized surface projections 92, 94, 96 may be representative of the different phases associated with the left ventricle in the heart of the patient.

Subsequently, at steps 98-100, these standardized surface projections 92, 94, 96 may be processed to generate a normal surface projection 102 corresponding to a particular phase associated with an anatomical region of interest. In one embodiment, the normal generator module 24 (see FIG. 3) may be employed to generate the normal surface projection. In other words, the plurality of standardized surface projections 92, 94, 96 may be configured to serve as inputs to the normal generator module 24. Also, an output of the normal generator module 24 may include the normal surface projection. In other words, there is many-to-one relationship between the surface projection generator module 78 and the normal generator module 24.

Referring now to step 98, a mean and a standard deviation for each point in each of the surface projections 92, 94, 96 may be computed. Subsequently, at step 100, a normal surface projection corresponding to each phase of the anatomical region of interest may be generated using the corresponding mean and standard deviation values. More particularly, each pixel in the normal surface projection may be configured to have a value corresponding to a mean value of the corresponding pixels in the plurality of standardized surface projections corresponding to the particular phase of an anatomical region of interest associated with the group under consideration. For example, if the group under consideration includes 40 samples, then each pixel in the normal surface projection may be configured to have a value representative of a mean value of all the 40 corresponding pixels in the standardized surface projections associated with the 40 subjects in the group. Additionally, a standard deviation for each pixel in this normal surface projection may also be computed. Reference numeral 102 may generally be representative of a normal surface projection corresponding to a phase of an anatomical region of interest in an organ.

Also, normal surface projections corresponding to the other phases of the anatomical region of interest may be generated. In addition, normal surface projections corresponding to different phases associated with other organs may also be generated. Furthermore, normal surface projections corresponding to each of the one or more groups of subjects may be generated.

Subsequently, these normal surface projections may be used to create a normal standardized data repository. In one embodiment, the normal data repository may include a normal standardized database 104. It may be noted that the terms normal standardized database and normal database may be used interchangeably.

This normal database 104 may then be used by the clinician to compare a current standardized surface projection with a corresponding normal surface projection stored in the normal database 104, thereby dramatically enhancing the comparison of the current surface projection and the stored normal surface projection to aid in the detection and/or diagnosis of a disease state. By implementing the normal database 104 as described hereinabove, surface projections corresponding to specific phases associated with various anatomical regions of interest in different organs may be generated, thereby allowing an enhanced comparison. Furthermore, the standardized surface projections are transformed to be aligned with a common reference plane, thereby substantially reducing occurrence of false positives and/or false negatives.

With returning reference to FIG. 3, image data obtained during a current imaging session may be processed via the image data acquiring module 20, the extractor module 74, the standardizer module 76, and the surface projection generator module 78 to generate a standardized surface projection corresponding to a phase of an anatomical region of interest. Subsequently, the diagnosis module 26 may be configured to facilitate detection and/or diagnosis of a disease state in the patient 12 under investigation. In other words, the diagnosis module 26 may be configured to retrieve a normal surface projection from the normal database 104 (see FIG. 4) corresponding to the current surface projection. Additionally, the diagnosis module 26 may be configured to compare the current surface projection and the corresponding retrieved normal surface projection to aid in the detection of a disease state, if any. More particularly, the diagnosis module 26 may be configured to retrieve a normal surface projection corresponding to a phase associated with the anatomical region of interest from the normal database 104 to facilitate comparison with a current standardized surface projection.

Referring now to FIGS. 5A-5E, a flow chart 110 illustrating an exemplary method of generating an exemplary normal data repository is presented. In accordance with exemplary aspects of the present technique, the normal data repository may be configured to include normal surface projections corresponding to different phases associated with anatomical regions of interest in various organs in groups of subjects. Moreover, the normal data repository so generated may be configured to aid in enhanced detection and/or diagnosis of a disease state in a patient. The method starts at step 114, where image data corresponding to different phases associated with a normal anatomical region of interest may be extracted from image data 112. It may be noted that the image data 112 may be representative of image data associated with a normal organ of a subject in a group. By way of example, if the normal scanned organ includes the heart, then the image data 112 includes image data corresponding to the heart of the subject. Subsequent to processing by step 114, image data corresponding to the plurality of phases of the heart, such as the systolic phase, the diastolic phase, and phases therebetween, may be obtained. Also, reference numeral 116 may generally be representative of image data corresponding to the plurality of phases associated with the normal scanned organ extracted at step 114. In a present example, the image data 116 corresponding to the plurality of phases of the normal scanned organ may include three-dimensional (3D) image volumes representative of the various phases of the normal scanned organ. Furthermore, although the present example describes the method with reference to real-time access of image data from the patient currently under observation, it may also be noted that the present technique may also find application with previously acquired data and/or archived data.

Subsequently, at step 118, image data corresponding to a region of interest within the normal scanned organ may be extracted from the 3D image volumes 116. Reference numeral 120 may be representative of the extracted image data corresponding to the various phases associated with the region of interest within the normal scanned organ. By way of example, if the normal scanned organ includes the heart, then a region of interest within the heart may include a left ventricle, for instance. Accordingly, in the present example, the extracted image data 120 may include image data corresponding to the various phases associated with the left ventricle.

Figure 6:
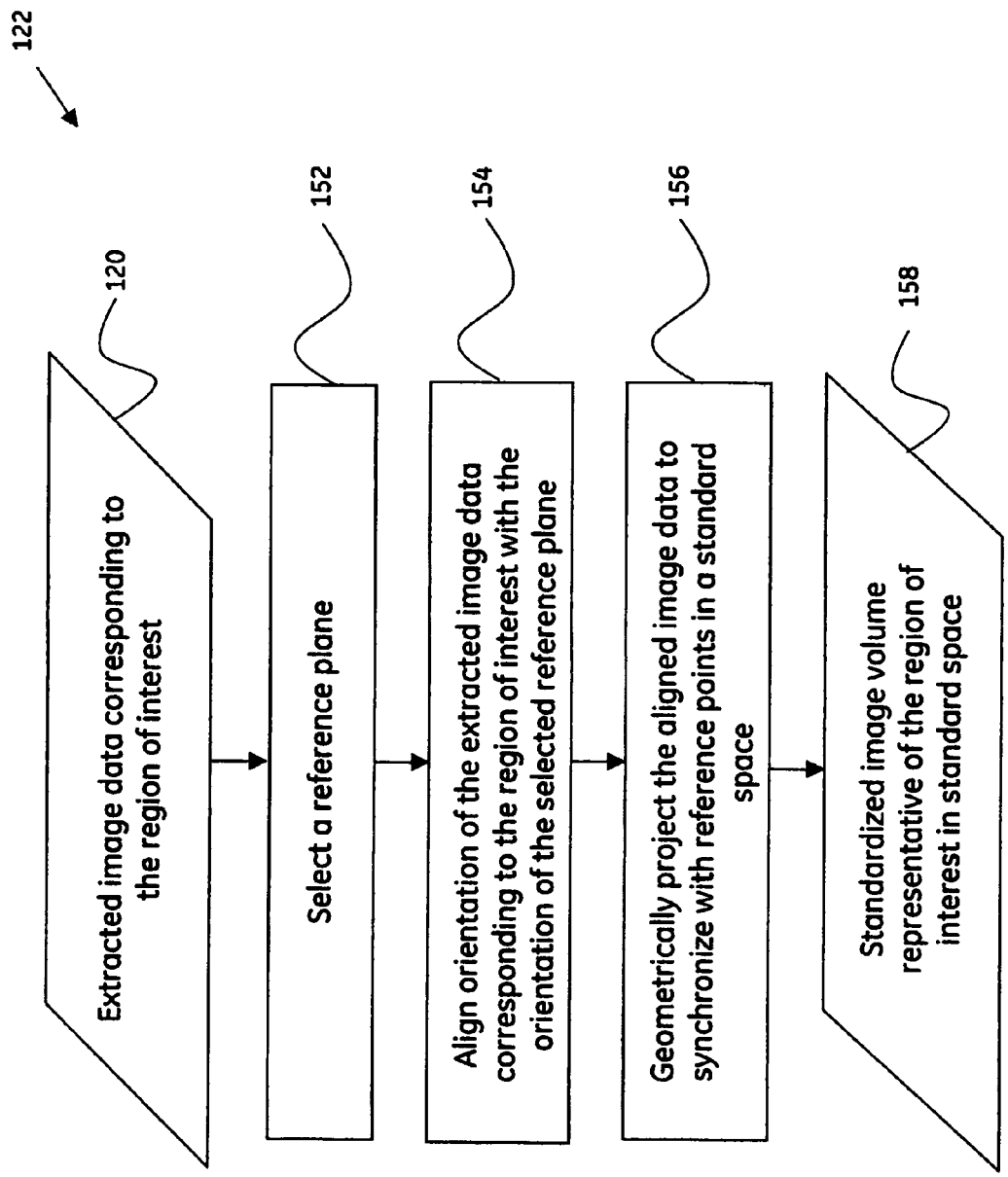
FIG. 6 is a flow chart illustrating an exemplary process of generating a standardized normal surface projection, in accordance with aspects of the present technique.

With continuing reference to FIG. 5, the extracted image data 120 may be standardized, as indicated by step 122. Step 122 may be better understood with reference to FIG. 6. Turning now to FIG. 6, a flow chart illustrating the standardization process of step 122 (see FIG. 5) is depicted. As previously noted, presently available techniques typically generate normal polar plots by averaging a plurality of polar plots corresponding to subjects in a group. However, these techniques fail to account for any variation in orientation of the anatomical regions of interest while generating the normal averaged polar plots. Use of these averaged polar plots for the detection of disease states may disadvantageously result in false positives and/or false negatives.

In accordance with exemplary aspects of the present technique, the failings of the presently available techniques may be circumvented by aligning the extracted image data 120 to have a common orientation. Accordingly, the extracted image data 120 may be transformed to have a common orientation. In other words, transformations may be applied to the extracted image data 120 to orient the extracted image data 120 into a standardized anatomical space. More particularly, the standardized surface projections may be oriented along a common orientation plane. The common orientation plane may also be referred to as a reference plane.

The method starts at step 152, where a reference plane is selected. In one embodiment, the reference plane may be selected from a standardized reference or atlas space. Subsequently, an orientation of the extracted image data 120 may be aligned with an orientation of the selected reference plane, as indicated by step 154. In other words, the extracted image data 120 may be transformed to orient the extracted image data 120 with an orientation of the selected reference plane. More particularly, the extracted image data 120 may be oriented along a common orientation plane, namely the selected reference plane. In one embodiment, each point in the aligned image data set may be subject to a transform in order to facilitate the alignment of the extracted image data set with the selected reference plane. For example, if a point in the extracted image data set includes (X, Y, Z) as its coordinates, then that point may be "standardized" or "aligned" to a common reference point by transforming its coordinates to a standardized point having (X+ΔX, Y+ΔY, Z+ΔZ) as its coordinates, thereby aligning the orientation of the point in the extracted image data set 120 with the orientation of the selected reference plane.

Subsequently, at step 156, the aligned image data set may be geometrically projected to synchronize the aligned image data set with one or more reference points in a standard space. It may be noted that the standard space may be indicative of a reference space or an atlas space. In other words, aligned image data set may be geometrically projected to orient the aligned image data set into a standardized anatomical space, thereby generating one or more "standardized" image data sets. In certain embodiments, the standardized image data sets obtained consequent to processing by step 156 may include a standardized image volume that is representative of the region of interest in standard space. The standardized image volume representative of the region of interest in the standard space may generally be represented by reference numeral 158. It may be noted that standardized image volumes corresponding to each phase associated with the region of interest may be generated.

With returning reference to FIG. 5, consequent to processing by step 122, standardized image volumes 158 (see FIG. 6) corresponding to the plurality of phases associated with the region of interest may be generated. Once the standardized image volumes 158 are generated, surface projections corresponding to each of the plurality of phases associated with the desired region of interest may be generated, as indicated by step 124. In one embodiment, the surface projections may include stereotactic surface projections. These surface projections may generally be represented by reference numeral 126. It may be noted that the surface projections 126 may be representative of the plurality of phases associated with the region of interest of one subject.

Subsequently, intensity values in the surface projection 126 may be normalized, as indicated by step 128. In other words, intensity values in the surface projection 126 may be normalized to a reference region in the surface projection 126. Consequent to processing at steps 122-128 standardized and normalized surface projections may be generated. Reference numeral 130 may generally be representative of these standardized and normalized surface projections.

In accordance with further aspects of the present technique, at step 132, such standardized and normalized surface projections may be generated for each of the one or more subjects in a group. More particularly, steps 114-128 may be repeated. The plurality of surface projections so generated at step 132 may generally be represented by reference numeral 134.

Further, at step 136, in accordance with aspects of the present technique, statistics corresponding to each point in each of the surface projections 134 may be computed. More particularly, a mean, a standard deviation, or a combination thereof, corresponding to each point in each of the plurality of standardized and normalized surface projections 134 associated with the group may be computed. Subsequently, at step 138, for a given group, a normal surface projection corresponding to each of the plurality of phases associated with the region of interest may be generated employing the mean, the standard deviation, or a combination thereof, computed at step 136. Consequent to step 138, a plurality of normal surface projections 140 corresponding to the plurality of phases of the region of interest for the particular group under consideration may be generated. As previously noted, the term "normal" surface projection is used to represent a surface projection representative of a normal anatomical region of interest within a normal anatomical organ.

In addition, normal surface projections corresponding each of the one or more groups may be generated, as indicated by step 142. In other words, steps 114-140 may be repeated for each of the one or more groups of subjects. Reference numeral 144 may be representative of the plurality of normal surface projections associated with the one or more groups. Subsequently, at step 146, these normal surface projections 144 may be employed to generate a normal reference database 148. It may be noted that the normal reference database 148 may be configured to include normal reference surface projections corresponding to the one or more groups, where each of the one or more groups includes one or more subjects. Also, each subject in each group may include a plurality of normal reference surface projections corresponding to the plurality of phases associated with various regions of interest in different organs. It may be noted that the normal database 148 may include the data repository 28 (see FIG. 1).

In accordance with exemplary aspects of the present technique, the normal database 148 is configured to include normal surface projections corresponding to various phases associated with anatomical regions of interest within one or more organs and corresponding to a plurality of groups of subjects, thereby facilitating enhanced detection and/or diagnosis of disease states. More particularly, the normal database 148 may be configured to include normal surface projections corresponding to the different phases and of the various normal anatomical regions of interest in one or more organs, thereby dramatically improving clinical workflow by aiding in enhanced detection and/or diagnosis of disease states. Additionally, since these normal surface projections include surface projections that are transformed to be aligned with a reference plane and standardized to a reference space, use of these normal surface projections in the detection and/or diagnosis of disease states may advantageously result in reducing occurrence of false positives and/or false negatives.

Figure 7A:
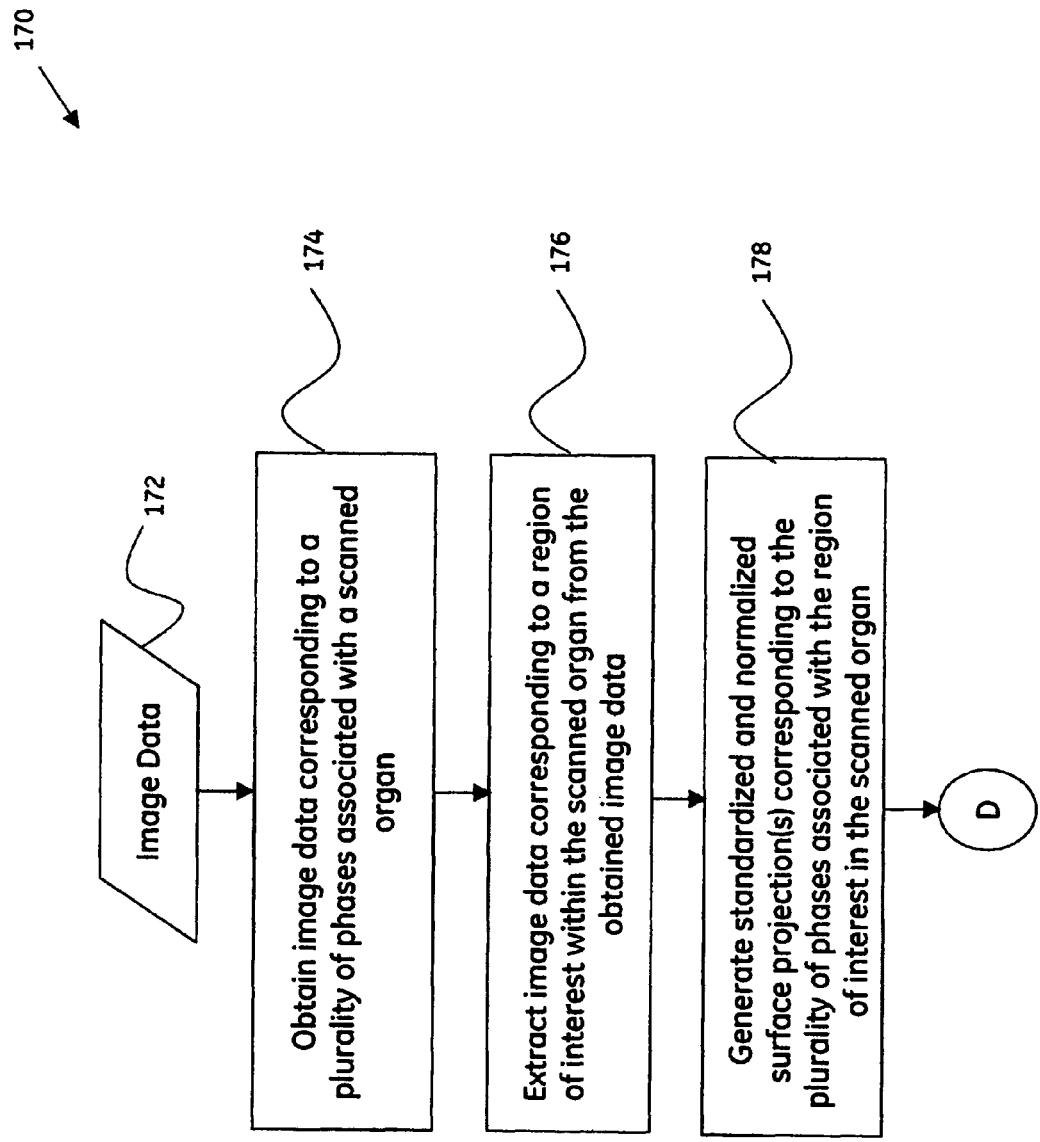
FIGS. 7A-7C are flow charts illustrating an exemplary process of diagnosing a disease state, in accordance with aspects of the present technique.
Figure 7B:
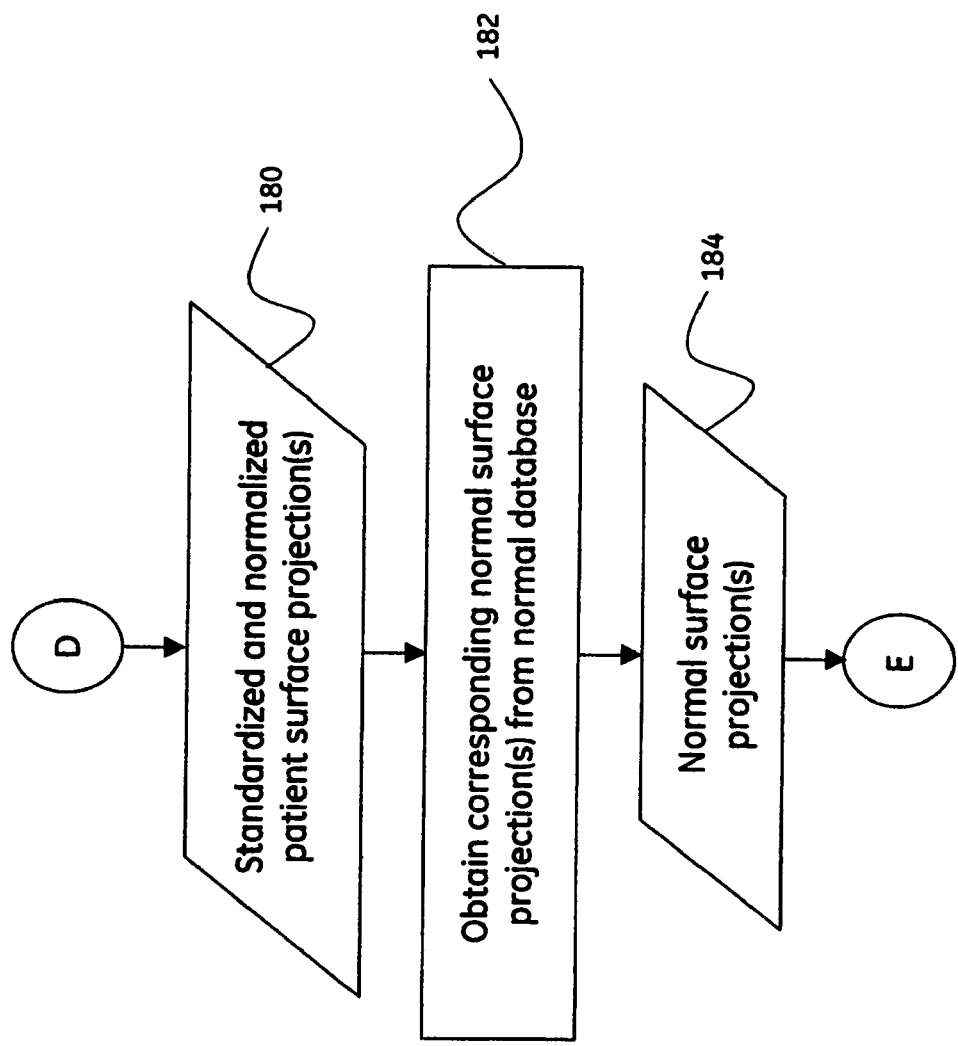
Figure 7C:
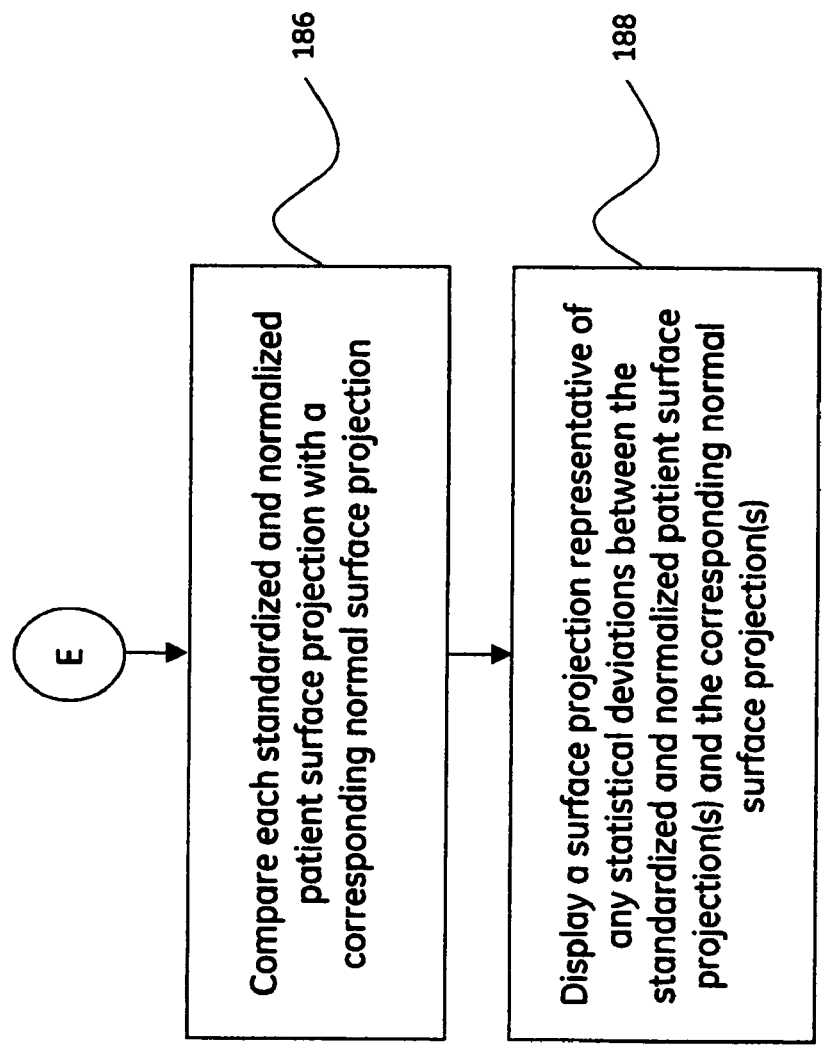

Accordingly, an exemplary method of diagnosing a disease state employing the normal database, such as the normal database 148 (see FIG. 5), is presented. FIGS. 7A-7C illustrate a flow chart 170 representing an exemplary method of detecting a disease state using the normal database 148 (see FIG. 5). The method starts at step 174 where image data corresponding to a plurality of phases associated with a region of interest within a scanned organ may be extracted from image data 172 corresponding to a patient currently under investigation. It may be noted that the image data 172 may be representative of image data corresponding to an organ being scanned in a patient currently under investigation. Also, in certain embodiments, the image data corresponding to the plurality of phases of the scanned organ may include three-dimensional (3D) image volumes representative of the various phases of the scanned organ obtained at step 174, as previously noted with reference to FIG. 5. Here again, although the present example describes the method with reference to real-time access of image data from the patient currently under observation, it may be noted that the present technique may also find application with previously acquired data and/or archived data.

Subsequently, at step 176, image data corresponding to a region of interest within the scanned organ may be extracted from the 3D image volumes. By way of example, if the scanned organ includes the heart, then a region of interest within the heart may include a left ventricle, for instance. Accordingly, in the present example, the extracted image data may include image data corresponding to the various phases associated with the left ventricle in the heart.

Moreover, at step 178, the extracted image data representative of the plurality of phases of the anatomical region of interest currently under investigation may be processed to generate a standardized and normalized surface projection 180 corresponding to each of the plurality of phases of the anatomical region of interest. More particularly, at step 178, a standardized and normalized surface projection 180 may be generated for each phase associated with the anatomical region of interest in the scanned organ of the patient. It may be noted that steps 122-130 (see FIG. 5) may be employed to generate the standardized and normalized surface projections 180 corresponding to the plurality of phases associated with the anatomical region of interest in the scanned organ of the patient under investigation.

Subsequently, it may be desirable to compare each of the current standardized and normalized surface projections 180 with a corresponding normal surface projection that has been previously generated and stored in the normal database 148 (see FIG. 5). Accordingly, the normal surface projections corresponding to the surface projections 180 may be retrieved from the normal database 148, as indicated by step 182. By way of example, if the current standardized surface projection 180 is representative of a systolic phase of the left ventricular region in the heart of a female patient of about 34 years of age under observation, then a normal reference surface projection corresponding to the systolic phase of the left ventricular region in the heart of a female patient of about 34 years of age may be retrieved from the normal database 148. The retrieved normal surface projection may generally be represented by reference numeral 184.

Figure 8A:
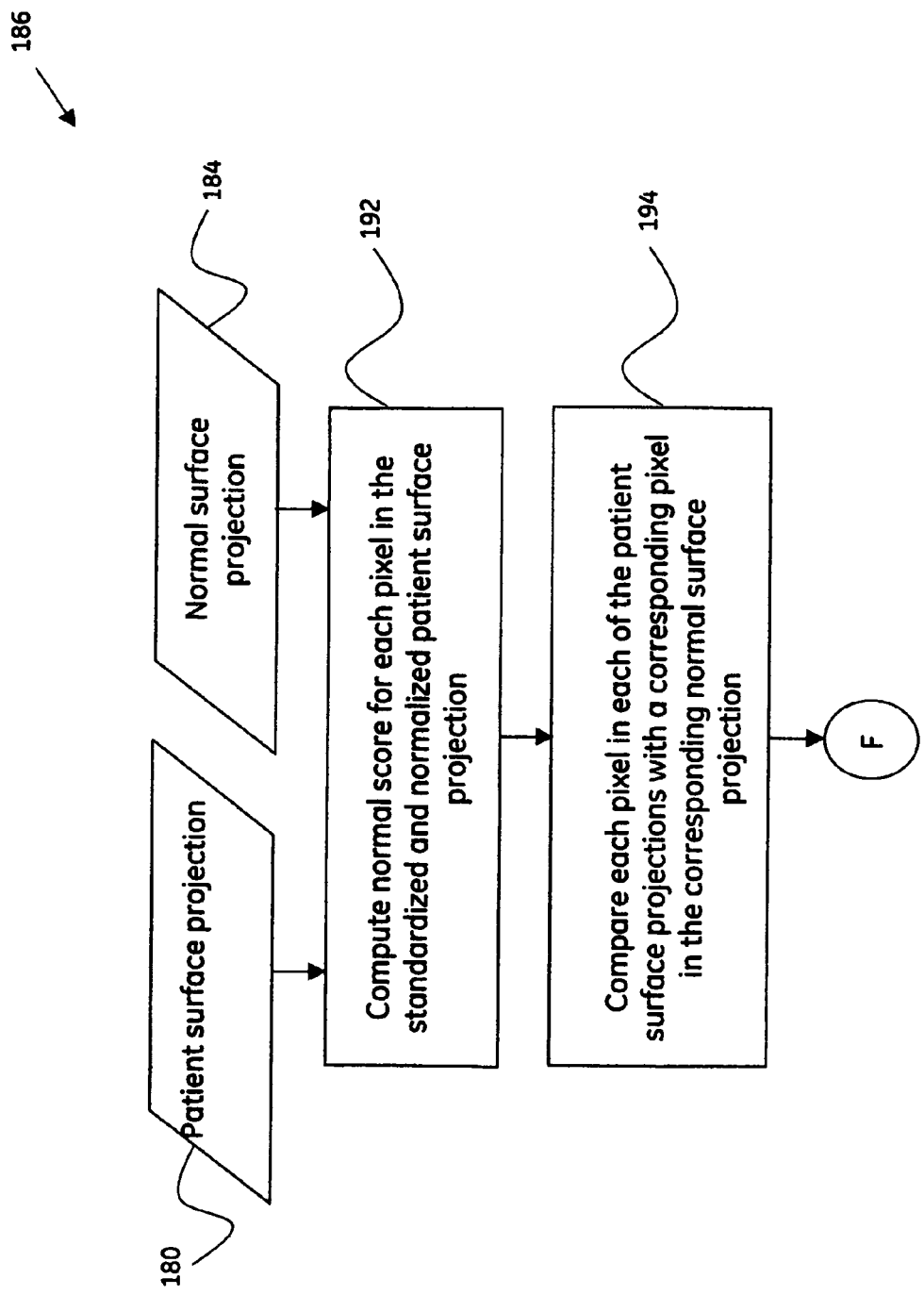
FIGS. 8A-8B are flow charts illustrating an exemplary process of comparing a current surface projection with a corresponding normal reference surface projection, in accordance with aspects of the present technique.
Figure 8B:
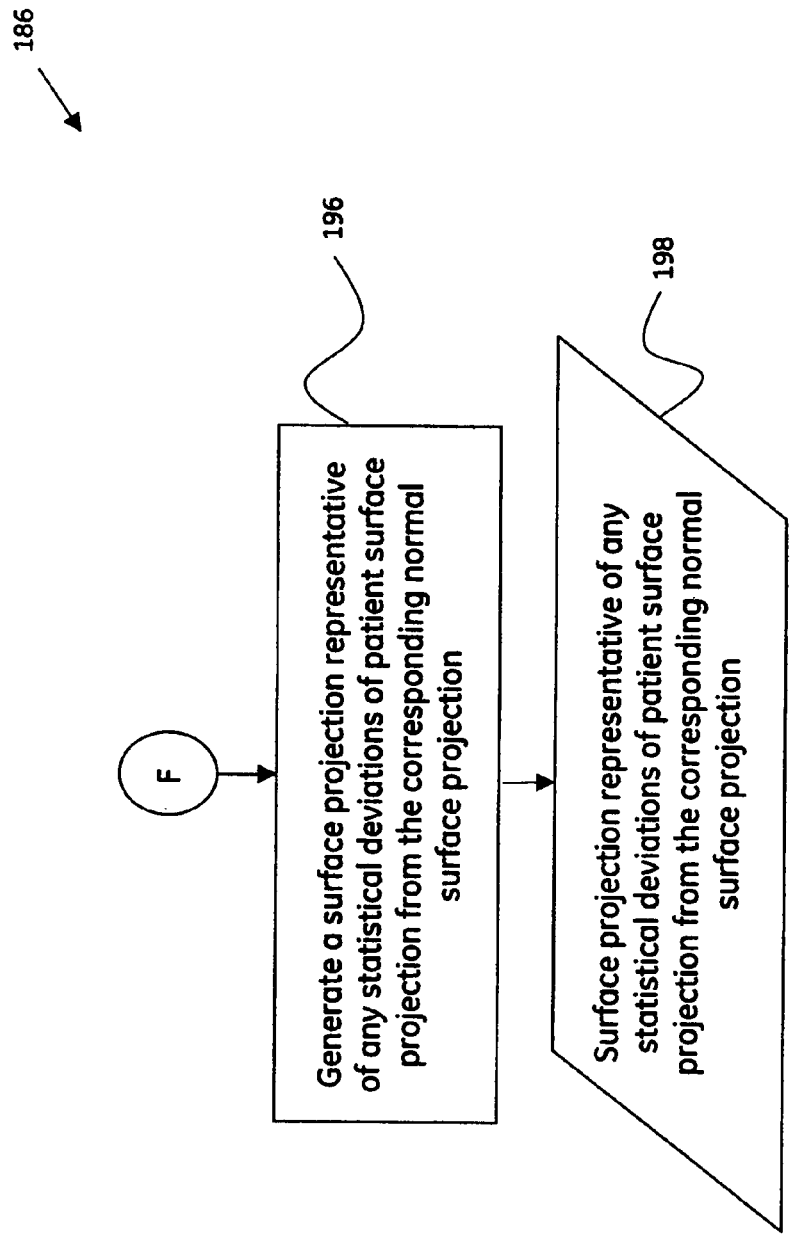

Furthermore, at step 186, the current standardized and normalized surface projection 180 may be compared with the corresponding normal surface projection 184. This comparison may be configured to aid the clinician in the detection and/or diagnosis of any disease states. Step 186 may be better understood with reference to FIGS. 8A-8B. Referring now to FIGS. 8A-8B, a flow chart illustrating an exemplary method of comparing the current standardized and normalized surface projection 180 with the corresponding normal surface projection 184 is presented. In accordance with exemplary aspects of the present technique, a pixel-by-pixel comparison of the current standardized and normalized surface projection 180 with the corresponding normal surface projection 184 may be conducted. More particularly, each pixel in the current standardized and normalized surface projection 180 may be compared with a corresponding pixel in the corresponding normal surface projection 184 to determine presence of any deviations from the normal surface projection 184, where the deviations may be indicative of a disease state.

In accordance with aspects of the present technique, a normal score for each pixel in the current standardized and normalized surface projection 180 may be computed. Accordingly, the method starts at step 192, where a normal score for each pixel in the current standardized and normalized surface projection 180 may be computed. In certain embodiments, the normal score may include a Z-score. Furthermore, in accordance with further aspects of the present technique, a Z-score of each pixel in the current standardized and normalized surface projection 180 may be computed using:

$$Z_{SCORE} = \frac{\hat{p} - \mu_{smtj\phi}}{\sigma_{smtj\phi}} \quad (1)$$

where $\hat{p}$ is a standardized patient vector,
$\mu_{smtj\phi}$ is the mean of the normal surface projection,
$\sigma_{smtj\phi}$ is the standard deviation of the normal surface projection,
s is indicative of the study (method of acquiring data),
m is indicative of the sex,
t is indicative of the tracer, such as Rubidium, Ammonia, Fluorodeoxyglucose (FDG), etc.,
j is indicative of a location of the anatomical region of interest, and
$\phi$ is indicative of the phase of the anatomical region of interest.

Subsequently, a pixel-by-pixel comparison of the current standardized and normalized surface projection 180 and the corresponding normal surface projection 184 may be carried out at step 194. As will be appreciated, assessment and functional significance of coronary artery disease (CAD) is typically done by measurement of two physiological measurements, namely myocardial perfusion using Ammonia [$^{13}$N] or Rubidium [$^{82}$Rb] under stress and resting conditions and myocardial viability using [$^{18}$F-FDG]. Accordingly, the detection of CAD may include comparison of the current standardized and normalized surface projection 180 with a healthy normal. In other words, the current standardized and normalized surface projection 180 may be compared with a corresponding normal surface projection 184 retrieved from the normal database 148 (see FIG. 5). Furthermore, as previously noted, these normal databases may be segregated on study type (stress/rest), tracer, and sex categories, in certain embodiments.

In accordance with exemplary aspects of the present technique, at step 194, the comparison of the current standardized and normalized surface projection 180 with the corresponding normal surface projection 184 may be carried out in a standardized domain. By way of example, different cardiac anatomies in the normal surface projection 184 may be mapped to this standard domain using rigid transformation techniques. Furthermore, by applying the inverse transformation of the rigid transformation, images from the patient 12 (see FIG. 1), such as the standardized and normalized surface projection 180 may be transformed to conform to the anatomy of the myocardium. This anatomical standardization, where the myocardium itself serves as the anatomical standard advantageously aids in bringing data from different individuals into a compatible form providing possibilities to perform individual-group and group-by-group comparisons between patients and normal controls. Once a comparison has been made, in accordance with exemplary aspects of the present technique, a surface projection 198 representative of any statistical deviations of the current standardized and normalized surface projection 180 from the corresponding normal surface projection 184 may be generated, as indicated by step 196.

With returning reference to FIG. 7, once the surface projection 198 representative of any statistical deviations of the current standardized and normalized surface projection 180 from the corresponding normal surface projection 184 is generated, the results of the comparison step, namely the surface projection 198 of statistical deviations of the current standardized and normalized surface projection 180 from the normal surface projection 184 may be presented to the clinician as indicated by step 188. In certain embodiments, the results of the comparison step 186 may be visualized on a display, such as the display 32 (see FIG. 1). Presenting the surface projection 198 representative of statistical deviations of the current standardized and normalized surface projection 180 from the corresponding normal surface projection 184 may be configured to provide the clinician categorized indices of severity in a simple and easy to understand workflow, thereby simplifying the clinical workflow and enhancing patient care. It may be noted that steps 182-188 may be repeated for each of the patient surface projections 180 generated at step 178.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java or in paradigms like Service Oriented Architecture. Such code, as will be appreciated by those of ordinary skill in the art, may be stored or adapted for storage on one or more tangible, machine readable media, such as on memory chips, local or remote hard disks, optical disks (that is, CDs or DVDs), or other media, which may be accessed by a processor-based system to execute the stored code. Note that the tangible media may include paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The method for detecting a disease state and the system for detecting a disease state described hereinabove dramatically simplify clinical workflow by advantageously allowing display of a surface projection representative of any statistical deviations of the current standardized and normalized surface projection from the corresponding normal surface projection, thereby aiding the clinician in the detection and/or diagnosis of a disease state. Furthermore, the techniques described hereinabove dramatically improve the sensitivity and productivity of the clinicians while diagnosing and/or treating disease states, such as coronary artery disease, for example. In addition, the detection and/or diagnosis of a disease state may be substantially enhanced as the three-dimensional (3D) normal surface projections are generated to include actual anatomical information provided by high-resolution images, such as PET images or CT images. These 3D normal surface projections are employed to aid in the comparison of a patient disease state with respect to the normal database.

The above-description of the embodiments of the method for diagnosing a disease state and the system for diagnosing a disease state have the technical effect of effectively displaying an image representative of statistical deviation of the current standardized and normalized surface projection from the corresponding normal surface projection, thereby substantially enhancing the clinical workflow and productivity of the caregivers and patient care.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for detecting a disease state, the method comprising:
creating a normal standardized data repository, wherein the normal standardized data repository comprises one or more normal reference surface projections, wherein the normal reference surface projections comprise anatomical information obtained from one or more groups at different phases corresponding to one or more regions of interest in a normal organ, wherein each of the one or more groups comprises one or more subjects having normal organs, and wherein the normal standardized data repository is configured to aid in the detection of a disease state.

2. The method of claim 1, wherein the normal organ comprises a dynamic organ, a static organ, or a combination thereof.

3. The method of claim 1, wherein the surface projection comprises a stereotactic surface projection.

4. The method of claim 1, further comprising obtaining image data representative of the different phases corresponding to the one or more regions of interest in the normal organs, and wherein the image data is based on emissive data corresponding to radioactive tracers.

5. The method of claim 1, wherein creating the normal standardized data repository comprises obtaining image data corresponding to a plurality of phases associated with the normal organ.

6. The method of claim 5, wherein creating the normal standardized data repository further comprises extracting image data corresponding to a region of interest within the normal organ from the obtained image data to generate one or more extracted image data sets corresponding to each of the plurality of phases associated with the region of interest in the normal organ.

7. The method of claim 6, further comprising standardizing the one or more extracted image data sets.

8. The method of claim 7, wherein standardizing the one or more extracted image data sets comprises:
selecting a reference plane in the normal organ;
aligning orientation of the extracted image data sets corresponding to the region of interest with the selected reference plane to generate one or more aligned image data sets; and
projecting the aligned image data sets to synchronize the aligned image data sets with one or more reference points in a standard space to generate standardized image data sets.

9. The method of claim 8, further comprising generating a standardized surface projection corresponding to each of the standardized image data sets associated with the plurality of phases of the region of interest in the normal organ.

10. The method of claim 9, further comprising normalizing the standardized surface projection corresponding to each of the plurality of phases associated with the region of interest in the normal organ to generate a standardized and normalized surface projection corresponding to each of the plurality of phases associated with the region of interest in the normal organ.

11. The method of claim 9, further comprising generating a standardized and normalized surface projection corresponding to each of the plurality of phases associated with the region of interest in the normal organ for each of the one or more subjects in the group.

12. The method of claim 11, further comprising computing a mean, a standard deviation, or a combination thereof, corresponding to each point in each of the plurality of standardized and normalized surface projections associated with the group.

13. The method of claim 12, further comprising generating a normal reference surface projection corresponding to each of the plurality of phases associated with the region of interest in the normal organ employing the corresponding computed mean, the computed standard deviation, or a combination thereof, wherein the normal reference surface projections are representative of the plurality of phases associated with the region of interest in the normal organ.

14. The method of claim 13, further comprising generating normal reference surface projections corresponding to each of the one or more groups.

15. The method of claim 14, further comprising generating a normal standardized data repository using the normal reference surface projections corresponding to the one or more groups.

16. The method of claim 15, further comprising using the normal standardized data repository to facilitate diagnosis of a disease state by comparing a standardized surface projection associated with a subject with a corresponding normal surface projection, wherein the normal surface projection is retrieved from the normal standardized data repository.

17. A method for detecting a disease state, the method comprising:
    obtaining image data corresponding to a plurality of phases associated with a normal organ from a plurality of normal subjects;
    extracting image data corresponding to a region of interest within the normal organ from the obtained image data to generate one or more extracted image data sets corresponding to each of the plurality of phases associated with the region of interest;
    standardizing the extracted image data sets to generate standardized image data sets;
    generating a standardized surface projection corresponding to each of the standardized image data sets associated with the region of interest for each of the plurality of phases for each of the plurality of normal subjects;
    normalizing the standardized surface projection corresponding to each of the standardized image data sets associated with the region of interest for each of the plurality of phases for each of the plurality of normal subjects to generate a standardized and normalized surface projection corresponding to each of the standardized surface projection associated with the region of interest for each of the plurality of phases for each of the plurality of normal subjects;
    computing a mean, a standard deviation, or a combination thereof, based on the generated standardized and normalized surface projections associated with each of the plurality of phases for the plurality of normal subjects; and
    generating a normal reference surface projection corresponding to each of the plurality of phases associated with the region of interest employing the corresponding computed mean, the computed standard deviation, or a combination thereof, wherein the normal reference surface projections are representative of the plurality of phases associated with the region of interest in the normal organ.

18. The method of claim 17, further comprising generating a normal standardized data repository using the normal surface projections corresponding to one or more groups of subjects having normal organs.

19. A method for detecting a disease state, the method comprising:
    obtaining image data corresponding to a plurality of phases associated with an organ from a subject;
    generating a standardized and normalized surface projection corresponding to each of the plurality of phases associated with the organ;
    obtaining a corresponding normal reference surface projection associated with each of the plurality of phases from a normal standardized data repository; and
    comparing each of the standardized surface projections with a corresponding normal reference surface projection to facilitate detection of a disease state.

20. The method of claim 19, wherein generating a standardized and normalized surface projection corresponding to each of the plurality of phases comprises:
    extracting image data corresponding to a region of interest within the organ from the obtained image data to generate one or more extracted image data sets corresponding to each of the plurality of phases associated with the region of interest in the normal organ;
    standardizing the extracted image data sets to generate standardized image data sets;
    generating a standardized surface projection corresponding to each of the standardized image data sets associated with the region of interest in the normal organ for each of the plurality of phases for the subject; and
    normalizing the standardized surface projection corresponding to each of the standardized image data sets associated with the region of interest for each of the plurality of phases for each of the plurality of normal subjects to generate a standardized and normalized surface projection corresponding to each of the standardized surface projection associated with the region of interest for each of the plurality of phases for each of the plurality of normal subjects.

21. The method of claim 19, wherein comparing the standardized and normalized surface projection with the corresponding normal reference surface projection comprises comparing each pixel in the standardized and normalized surface projection with a corresponding pixel in the normal reference surface projection to detect presence of any deviations of the standardized and normalized surface projection from the corresponding normal reference surface projection, wherein the deviations are indicative of a disease state.

22. The method of claim 21, wherein comparing each pixel in the standardized and normalized surface projection with a corresponding pixel in the normal standardized surface projection comprises:
    computing a normal score corresponding to each pixel in the standardized and normalized surface projection; and
    generating a surface projection representative of a statistical deviation of the standardized and normalized surface projection from the corresponding normal reference surface projection.

23. The method of claim 22, further comprising displaying the surface projection representative of a statistical deviation of the standardized and normalized surface projection from the corresponding normal reference surface projection on a display to aid a clinician in the detection or diagnosis of a disease state.

24. A processing platform, comprising:
an image data acquiring module configured to acquire image data corresponding to a plurality of phases associated with an organ;
a segmentation module configured to:
extract image data corresponding to a region of interest in the organ from the obtained image data to generate one or more extracted image data sets corresponding to each of the plurality of phases associated with the region of interest in the organ;
standardize the extracted image data sets to generate standardized image data sets;
generate a standardized surface projection corresponding to each of the standardized image data sets associated with the region of interest in the organ for each of the plurality of phases for the subject;
normalize the standardized surface projection corresponding to each of the standardized image data sets associated with the region of interest in the organ for each of the plurality of phases for the subject to generate a standardized and normalized surface projection corresponding to each of the standardized image data sets associated with the region of interest in the organ for each of the plurality of phases for the subject;
a normal generator module configured to:
generate a normal reference surface projection corresponding to each of the plurality of phases using the standardized and normalized surface projections;
generate a normal standardized data repository using the normal reference surface projections, wherein the normal standardized data repository comprises one or more normal reference surface projections; and
a diagnosis module configured to aid in comparing a standardized and normalized surface projection associated with a current subject with a corresponding normal reference surface projection to facilitate detection of a disease state, wherein the diagnosis module is configured to generate a surface projection representative of any statistical deviation of the current standardized and normalized surface projection from the corresponding normal reference surface projection.

25. A system, comprising:
an imaging system configured to aid in acquisition of image data, wherein the image data is representative of an organ in a subject;
a processing platform configured to aid in processing the acquired image data, comprising:
an image data acquiring module configured to acquire image data corresponding to a plurality of phases associated with the organ;
a segmentation module configured to:
extract image data corresponding to a region of interest in the organ from the obtained image data to generate one or more extracted image data sets corresponding to each of the plurality of phases associated with the region of interest in the organ;
standardize the extracted image data sets to generate standardized image data sets;
generate a standardized surface projection corresponding to each of the standardized image data sets associated with the region of interest for each of the plurality of phases for the subject;
normalize the standardized surface projection corresponding to each of the standardized image data sets associated with the region of interest in the organ for each of the plurality of phases for the subject to generate a standardized and normalized surface projection corresponding to each of the standardized image data sets associated with the region of interest in the organ for each of the plurality of phases for the subject;
a normal generator module configured to:
generate a normal reference surface projection corresponding to each of the plurality of phases using the standardized and normalized surface projections;
generate a normal standardized data repository using the normal reference surface projections, wherein the normal standardized data repository comprises one or more normal reference surface projections;
a diagnosis module configured to aid in comparing a standardized and normalized surface projection associated with a current subject with a corresponding normal reference surface projection to facilitate detection of a disease state, wherein the diagnosis module is configured to generate a surface projection representative of any statistical deviation of the current standardized and normalized surface projection from the corresponding normal reference surface projection; and
a display module configured to display the standardized and normalized surface projection, the normal reference surface projection, the surface projections representative of any statistical deviation of the current standardized and normalized surface projection from the corresponding normal reference surface projection, other image data, or combinations thereof, to aid a clinician in the detection of a disease state.

* * * * *